United States Patent [19]

Swerdloff et al.

[11] Patent Number: 5,351,280
[45] Date of Patent: Sep. 27, 1994

[54] MULTI-LEAF RADIATION ATTENUATOR FOR RADIATION THERAPY

[75] Inventors: Stuart Swerdloff; Thomas R. Mackie; Timothy Holmes, all of Madison, Wis.

[73] Assignee: Wisconsin Alumni Research Foundation, Madison, Wis.

[21] Appl. No.: 71,743

[22] Filed: Jun. 9, 1993

Related U.S. Application Data

[63] Continuation-in-part of Ser. No. 865,521, Apr. 9, 1992.

[51] Int. Cl.$^5$ .............................................. A61N 5/10
[52] U.S. Cl. ..................................... 378/65; 378/150; 378/151; 378/162
[58] Field of Search ........................... 378/65, 150–153

[56] References Cited

U.S. PATENT DOCUMENTS

| | | | |
|---|---|---|---|
| 4,754,147 | 6/1988 | Maughan et al. | 250/505.1 |
| 4,794,629 | 12/1988 | Pastyr et al. | 378/152 |
| 4,817,125 | 3/1989 | Sklebitz | 378/152 |
| 4,868,843 | 9/1989 | Nunan | 378/152 |
| 4,868,844 | 9/1989 | Nunan | 378/152 |
| 4,905,268 | 2/1990 | Mattson et al. | 378/158 |
| 4,987,309 | 1/1991 | Klasen et al. | 250/492.1 |
| 4,998,268 | 3/1991 | Winter | 378/63 |
| 5,012,506 | 4/1991 | Span et al. | 378/152 |

OTHER PUBLICATIONS

Calculation and Application of Point Spread Functions for Treatment planning with High Energy Photon Beams, *Acta Oncologica* 26 (1987) pp. 49–56, A. Ahnesjo, et al.
Methods of Image Reconstruction from Projections Applied to Conformation Radiotherapy, *Phys. Med. Biol.*, 1990, vol. 35, No. 10, 1423–1434, Bortfeld, et al.
Feasibility Solutions in Radiation Therapy Treatment Planning, *Dept. of Radiation Therapy*, Univ. of Pa. School of Med., pp. 220–224, Altschuler, et al. (1984).
A Primer on Theory & Operation of Linear Accelerators in Radiation Therapy, *Medical Physics Pub. Corp.*, (1981) C. J. Karzmark, et al.
The Accuray Neutron 1000, A Medical Systems for Frameless Stereotoxic Radiosurgery, Accuray, Inc., J. R. Adler, et al., May 1992.
Optimization of Stationary and Moving Beam Radiation Therapy Techniques, *Radiotherapy and Ocology*, 12 (1988) 129–140, A. Brahme.
A Unified Approach to the Optimization of Brachytherapy and External Beam Dosimetry, *Int. J. Radiation Ocology Biol. Phys.*, vol. 20 pp. 859–873, Holmes, et al. (1991).
Optimization of Conformal Radiotherapy Dose Distributions by Simulated Annealing, *Phys. Med. Biol.*, vol. 34, No. 10, 1349–1370, S. Webb (1989).
A Constrained Least-Squared Optimization Method for External Beam Radiation Therapy Treatment Planning, (List continued on next page.)

*Primary Examiner*—Craig E. Church
*Attorney, Agent, or Firm*—Quarles & Brady

[57] ABSTRACT

A radiation therapy apparatus includes a multi-leaf attenuator having a first plurality of radiation attenuating leaves and a second plurality of radiation attenuating leaves. The first plurality of leaves is spaced with gaps between adjacent leaves within a radiation beam so that the leaves and the gaps therebetween divide the radiation beam into rays. The second plurality of leaves is disposed directly under gaps in the first plurality of leaves so that each ray of the beam can be occluded by a leaf in either the first or second plurality. The gaps eliminate interference between leaves; the staggering prevents radiation leakage between leaves. Each leaf, in both groups, may be moved between a first open state on one side of the beam, a closed state within the beam thus occluding one ray of the beam, and a second open state on the other side of the beam. By controlling the duty cycle of the leaves between the open and closed states, each ray of the beam may be effectively and individually attenuated over a range of intensities. Attenuating the motion between two open states provides more even radiation exposure.

17 Claims, 10 Drawing Sheets

OTHER PUBLICATIONS

*Med. Phys.* 11(5), Sep./Oct. 1984 pp. 659–664, G. Starkschall.

On the Use of Cimmino's Simulataneous Projections Method for Computing a Solution of the Inverse Problem in Radiation Therapy Treatment Planning, *Inverse Problems*, 4 (1988) 607–623, Y. Gensor, et al.

Tomotherapy: A New Concept for the Delivery of Conformal Radiotherapy using Dynamic Compensation, Jul. 1992, Swerdloff, et al.

Progress In Medical Radiation Physics vol. 2, 1985, added by Colin Orton, Plenum Press, W. A. Jennings pp. 1–111.

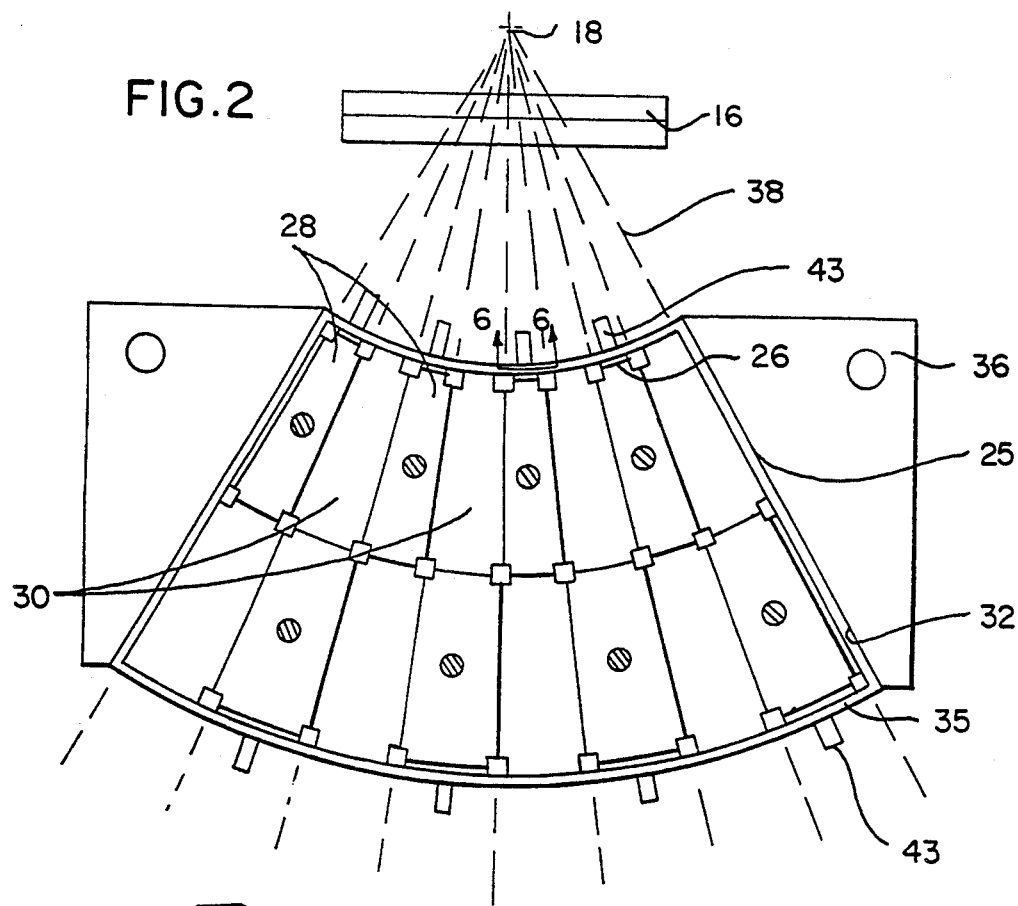
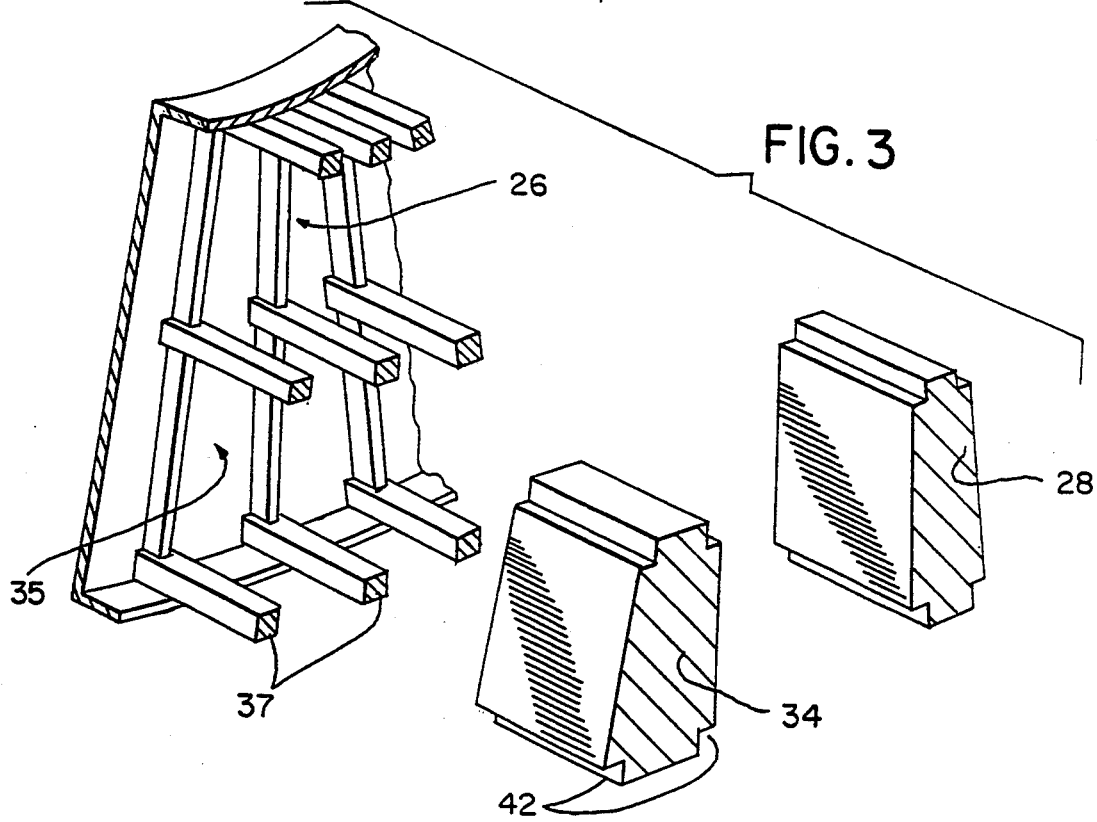

FIG. 4A
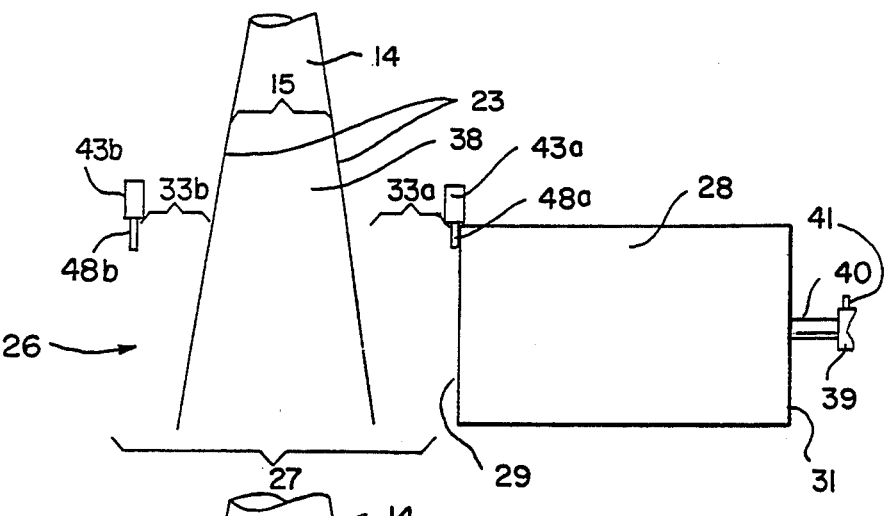
FIG. 4B
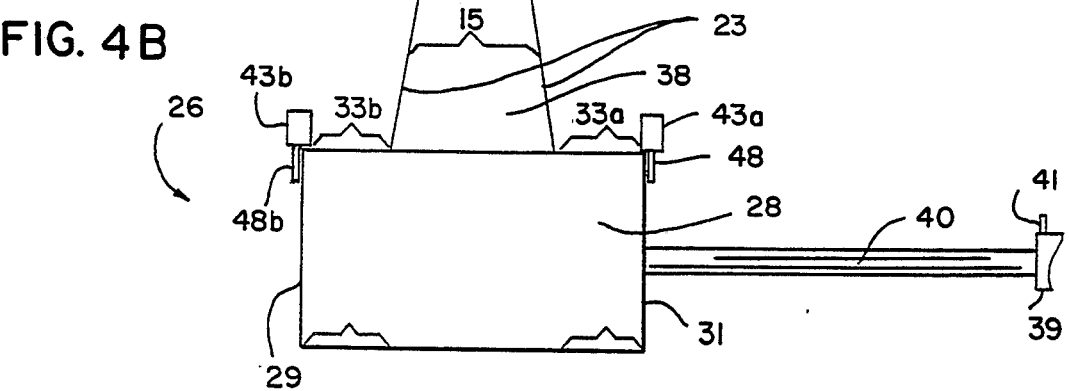
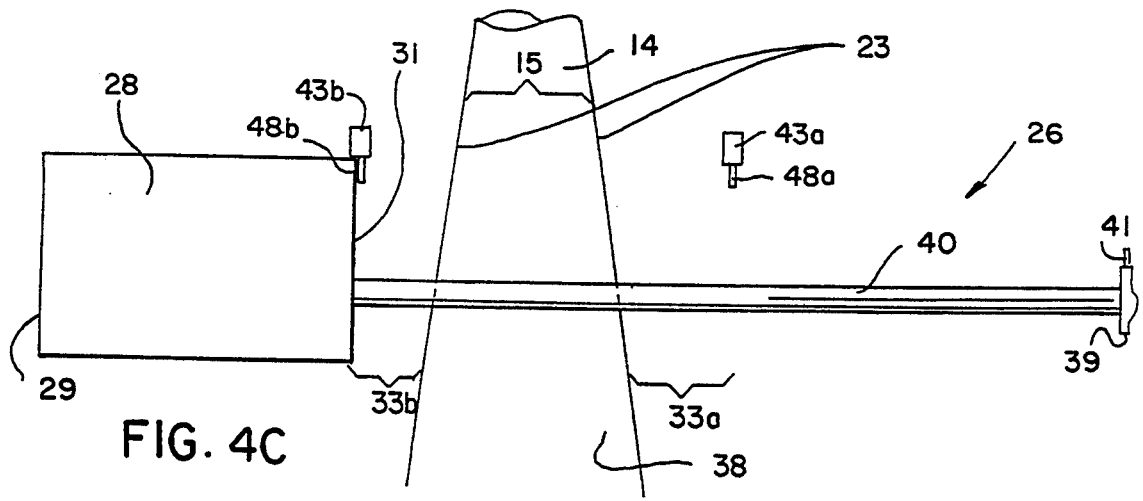
FIG. 4C

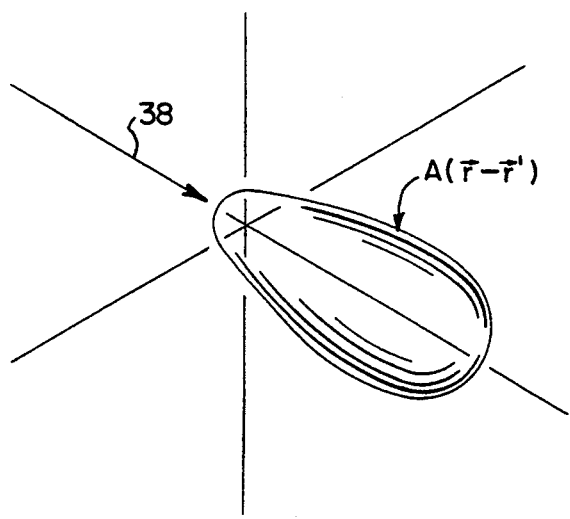
FIG. 10
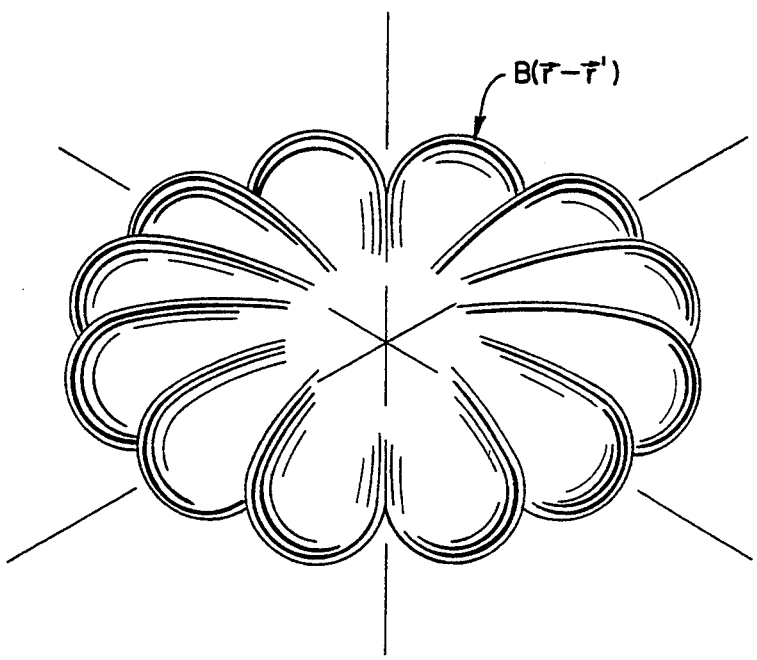
FIG. 11
FIG. 9
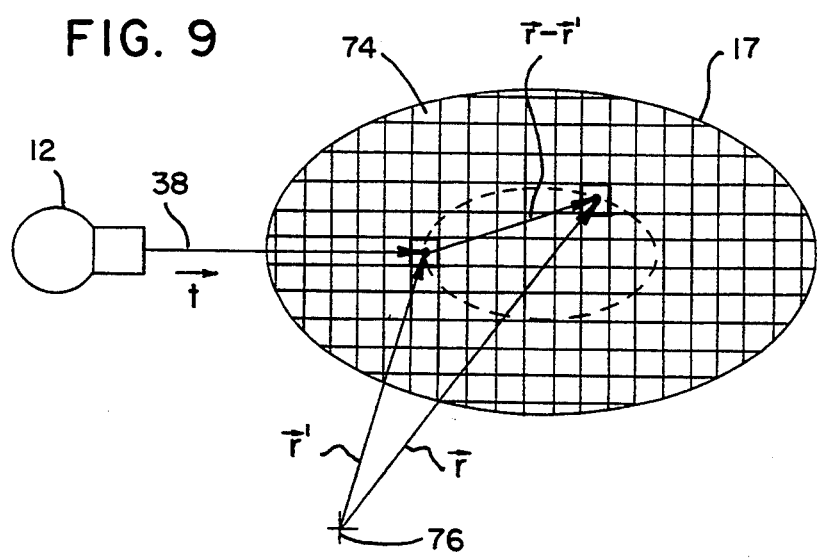

MULTI-LEAF RADIATION ATTENUATOR FOR RADIATION THERAPY

This invention was made with Unites States Government support awarded by the National Institute of Health (NIH), Grant Nos. NCI R29 CA48902 and NIH Training Grant NRSA CA09206. The United States Government has certain rights in this invention.

This application is a continuation in part of a patent application Ser. No. 07/854,521 filed Mar. 19, 1992, entitled "Method & Apparatus For Radiation Therapy".

FIELD OF THE INVENTION

This invention relates generally to radiation therapy equipment for the treatment of tumors, or the like, and specifically to a mechanism for regulating the dose of radiation within irregularly shaped zones within a patient.

BACKGROUND ART

Medical equipment for radiation therapy treats tumorous tissue with high energy radiation. The dose and the placement of the dose must be accurately controlled to insure both that the tumor receives sufficient radiation to be destroyed, and that damage to the surrounding and adjacent non-tumorous tissue is minimized.

Internal-source radiation therapy places capsules of radioactive material inside the patient in proximity to the tumorous tissue. Dose and placement are accurately controlled by the physical positioning of the isotope. However, internal-source radiation therapy has the disadvantages of any surgically invasive procedure, including discomfort to the patient and risk of infection.

External-source radiation therapy uses a radiation source that is external to the patient, typically either a radioisotope, such as $^{60}$Co, or a high energy x-ray source, such as a linear accelerator. The external source produces a collimated beam directed into the patient to the tumor site. External-source radiation therapy avoids some of the problems of internal-source radiation therapy, but it undesirably and necessarily irradiates a significant volume of non-tumorous or healthy tissue in the path of the radiation beam along with the tumorous tissue.

The adverse effect of irradiation of healthy tissue may be reduced, while maintaining a given dose of radiation in the tumorous tissue, by projecting the external radiation beam into the patient at a variety of "gantry" angles with the beams converging on the tumor site. The particular volume elements of healthy tissue, along the path of the radiation beam, change, reducing the total dose to each such element of healthy tissue during the entire treatment.

The irradiation of healthy tissue also may be reduced by tightly collimating the radiation beam to the general cross section of the tumor taken perpendicular to the axis of the radiation beam. Numerous systems exist for producing such a circumferential collimation, some of which use multiple sliding shutters which, piecewise, may generate a radio-opaque mask of arbitrary outline.

As part of collimating the beam to the outline of the tumor, the offset of the radiation beam, with respect to a radius line between the radiation source and the center of rotation of the radiation source, may be adjusted to allow the treated area to be other than at the center of rotation. Simultaneously changing the offset and the width of the radiation beam as a function of gantry angle allows tumorous tissue having an irregular cross-section within a plane parallel to the radiation beam to be accurately targeted. The width and offset of the radiation beam may be controlled by the use of a multiple-leaf circumferential collimator.

Adjustment of the offset and size of the radiation beam at various gantry angles allows considerable latitude in controlling the dose. Nevertheless, even using these techniques, there is still a considerable amount of undesired dose imparted to healthy tissue, especially where a treatment volume is concave or highly irregular within the plane parallel to the radiation beam.

A radiotherapy machine providing much reduced irradiation of healthy tissue is presented in co-pending U.S. patent application Ser. No. 07/865,521, by Stuart Swerdloff et al, filed Mar. 19, 1992. That application discloses the use of a number of radiation attenuating leaves in a rack positioned within the radiation beam before the beam enters the patient. The leaves slide into the radiation beam in a closed state and out of the radiation beam in an open state to allow unobstructed passage of a given ray of the beam ray. By controlling the ratio of time spent in the open and closed states, each ray may be attenuated over a continuous range of intensities. This ability to control not just the outline of the radiation but the intensity of each individual ray allows extremely precise control of the irradiation volume.

The radiation attenuating compensator described above must be capable of completely attenuating every ray of the fan beam. A single uncontrolled ray that leaks past the compensator to a patient will provide undesirable exposure to organs and other tissue including tissues outside a targeted treatment volume. Passage of unattenuated rays is avoided by using leaves with finely machined adjacent faces that can pass very close to each other minimizing the gap size between adjacent leaves minimizing leakage.

However, in practice, regardless of accurate machining techniques, small gaps between the leaves, that allow unattenuated rays to pass, are needed to prevent frictional contact. The exacting tolerances necessary to minimize the size of the leaf gaps are costly and such high tolerance components are prone to failure.

Another problem with the compensator described above is that the rays are not uniformly attenuated by the moving leaves because the leaves cannot be moved instantaneously. A leaf initially occludes the entire depth of its associated ray within the beam. As the leaf begins to move out of the beam, part of the ray is occluded and another part is left unobstructed. Eventually, the entire ray is unobstructed. The same non-uniform beam attenuation is again encountered when the leaf moves back into the beam.

This gradation in attenuation can be minimized by equipping the compensator with more powerful actuators to drive the leaves in and out of the fan beam width more rapidly. Bigger actuators, however, are more costly to utilize and maintain. Alternatively thinner leaves may be used which are light weight so that they can be moved more quickly. This, however, demands more actuators, creates more leaf gaps, and must be accommodated by a much more complicated control system.

SUMMARY OF THE INVENTION

The first embodiment of the present invention is a multi-leaf compensator for use in radiation therapy that moves two sets of leaves in and out of a radiation beam to produce a plurality of rays with independently adjustable fluence and a uniform fluence within each ray.

Specifically, the compensator incorporates a first set of attenuating leaves and a second set of attenuating leaves. The first set is supported by a first supporting structure for the guiding of the first set of leaves between a closed state, thus occluding every other ray of the beam and an open state outside of the radiation beam. A second support structure guides the second set of leaves between a closed state, each leaf occluding those rays of the beam not occluded by the first set of leaves when the latter are in the closed state and, an open state outside the radiation beam. A first plurality of leaves in the closed state are positioned closer to the radiation source than the second plurality of leaves in the closed state. Again, a motivation means moves each leaf between the open and closed states independently and a timing means controls the ratio of the period of time during which each leaf is in the closed state to the period of time during which each leaf is in the open state to control the average fluence of each ray of the beam.

It is thus one object of the invention to provide a compensator that eliminates the possibility of radiation leakage between the leaves of the compensator without requiring high tolerance machining or risking the possibility of interference between adjacent leaves. The use of two levels increases the spacing between the leaves eliminating their interference yet allows a slight overlap between the leaves of the two levels to eliminate passage of unintended radiation.

In a second embodiment, the compensator includes a number of radiation attenuating leaves orientated by a supporting structure that guides each leaf between a closed state centered within the radiation beam (the leaf including one ray of the beam) and an open state with the leaf displaced outside the radiation beam on a first side of the ray or a second open state with the leaf displaced outside the radiation beam on a second side. A motivation means independently moves each leaf alternately between an open and first closed state and between the open and second closed state. A timing means communicating with the motivation means controls the ratio of the period of time during which each leaf is in the closed state to the period of time during which each leaf is in either the first or second open states and thus controls the average fluence of each ray of the beam. This second embodiment of the invention can be used with either a single set or a double set of attenuating leaves.

It is thus another object of the invention to provide a compensator that attenuates individual rays of a high energy fan beam to provide uniform attenuation across the thickness of the fan beam. Provided the acceleration and velocity of the leaf in each direction is identical, the uneven radiation caused by motion of the leaf in one direction is canceled by the radiation caused by the motion of the leaf in the second direction.

The foregoing and other objects and advantages of the invention will appear from the following description. In the description, reference is made to the accompanying drawings which form a part hereof and in which there is shown by way of illustration several preferred embodiments of the invention. Such embodiments do not necessarily represent the full scope of the invention, however, and reference must be made therefore to the claims herein for interpreting the scope of the invention.

BRIEF DESCRIPTION OF THE DRAWINGS

FIG. 2 is a cross-section of the compensator assembly of FIG. 1 along line 2—2 showing both levels of compensator leaves, the trapezoidal aspect of each compensator leaf, the associated solenoid stopping assemblies, and the guide rails for supporting the compensator leaves when they move;

FIG. 3 is a cutaway perspective view of a set of guide rails and one leaf from the first level and one leaf from the second level of FIG. 1;

FIGS. 4(a)-(c) are side views of a leaf showing the relationship between a leaf, the beam and the solenoid assemblies when the leaf is in the first open FIG. 4(a), closed FIG. 4(b) and second open FIG. 4(c) states;

FIG. 9 is a diagrammatic representation of a patient receiving radiation therapy, showing the scatter kernel and the coordinate system used to describe the present invention;

FIG. 10 is a perspective representation of a monodirectional scatter kernel associated with a radiation beam at one gantry angle;

FIG. 11 is a perspective representation of a composite multidirectional scatter kernel associated with a plurality of radiation beams at multiple gantry angles;

DETAILED DESCRIPTION OF THE PREFERRED EMBODIMENT

Figure 1:
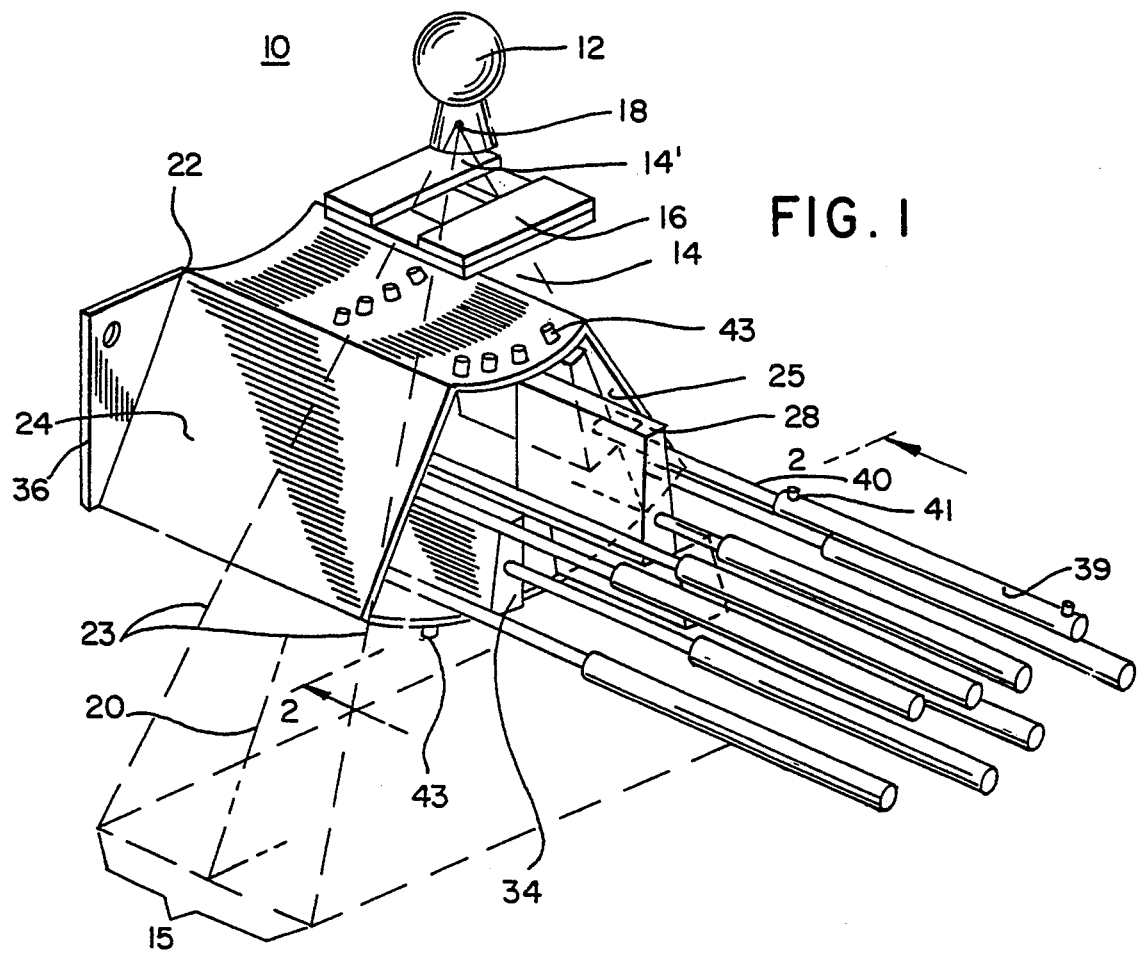
FIG. 1 is a perspective view of the compensator assembly used in the present invention showing both levels of the compensator leaves, their associate pneumatic cylinders and their associated solenoid assemblies.

Referring to FIG. 1, a radiation therapy unit 10 suitable for use with the present invention includes a radiation source 12 producing a generally conical radiation beam 14' emanating from a focal spot 18 and directed towards a patient (not shown). The conical beam 14' is collimated by a radiation opaque mask 16 constructed of a set of rectangular collimator blades to form a generally planar fan beam 14 centered about a fan beam plane 20.

I. The Compensator

Referring still to FIG. 1, a compensator 22 is centered in the fan beam 14 and about the fan beam plane 20, prior to the radiation being received by the patient. The compensator 22 includes a rack 24 having an upper level 25 that extends on both sides of the beam 14, past edges 23 of its thickness 15.

Referring to FIG. 2 the upper level 25 of the rack 24 has a set of sleeves 26 that slidably receive a corresponding number of equispaced trapezoidal leaves 28. Each leaf 28 is constructed of a dense, radio-opaque material such as lead, tungsten, cerium, tantalum or a related alloy.

The sleeves 26 are constructed of radio-translucent materials and integrally attached to a mounting plate 36 which is fixed relative to the focal spot 18. The mounting plate 36 is constructed of a sturdy radio-opaque material and is positioned outside the fan beam 14 to prevent interference with the fan beam 14.

The leaves 28, of the upper level together form an arc of constant radius about the focal spot 18. When the leaves 28 are in the closed position, a leaf gap 30 slightly less than the width of one leaf 28 exists between each two adjacent leaves 28. The leaves 28 and leaf gaps 30 divide the fan beam 14 into a set of adjacent slab like rays 38 at offset angles $\Phi$. The rays 38 that fall on the leaves 28 are attenuated and those directed between the leaves 28 are passed through the upper level 25 unattenuated.

Referring to FIGS. 1 & 2, the rack 24 also includes a lower level 32 that also extends past the edges of the thickness 15 of the beam 14. Lower level 34 is disposed between the upper level 25 and the patient. Like the upper level 25, the lower level 32 has a second set of sleeves 35 that receive a corresponding second number of equispaced trapezoidal leaves 34. Leaves 34 are constructed of the same material as leaves 28.

Each sleeve 35 of the second rack 32 is disposed under a leaf gap 30 in the upper level 25 and is centered within beam 14. Each leaf 34 in the lower level 32 is sized to overlap any flanking leaves 28 above it so that when viewed from the focal spot 18 it eliminates radiation leakage. The overlap, however, of leaves 28 in the upper level 25 and those in the lower level 32 is slight so that very few rays 38 are attenuated by leaves in both racks. The leaves 28, 34 of both levels are substantially the same thickness, or at least thick enough to entirely occlude their associated rays 38 when in the closed position.

Referring now to FIGS. 1 and 4(a)–(c), the sleeves 26, of both levels 25 are sized to permit each leaf 28 to slide to either side of the fan beam 14 completely out of the path of the fan beam 14 yet to still be guided by the sleeve 26. The sleeve 26, guides the leaf 28, between a "first open state" (FIG. 4(a)), wherein the leaf 28 is positioned to one side of the beam 14 allowing unobstructed passage of one ray 38 of the beam, and a "closed state" (FIG. 4(b)) in which the leaf 28 is positioned in the center of the sleeve 26 occluding one ray 38 of the beam, and a "second open state" (FIG. 4(c)), in which the leaf 28 on the opposite side of the beam 14 allowing unobstructed passage of the ray 38 of the beam.

Referring now to FIG. 3, the leaves 28, 34 are supported and guided within the sleeves 26, 35 by guide rails 37 fitted into notches 42 cut along the edges of the leaves 28, 34. The notches 42 allow the guide rails 37 to slidably retain the leaves 28, 34 within the sleeves 26, 35 during motion between the two open and single closed states.

Referring again to FIG. 1, each leaf 28 and 34 may be moved rapidly between its open and closed states by means of a corresponding pneumatic cylinder 39 connected to the leaf 28 and 34 by a flexible link 40. The pneumatic cylinders 39 have internal pistons (not shown) that may be moved at high velocity between the ends of the cylinders 39 by means of pressurized air coupled to the cylinders 39 through supply hoses 41. The supply hoses 41 are fed by a compensator control (not shown in FIGS. 1 or 2) to be described below. The pneumatic cylinders 39 are capable of applying high forces to the leaves 28, 34 to move them rapidly and independently between the closed and both open states.

As best seen in FIGS. 1 & 2, two solenoid stops 43 are associated with each leaf 28, 34. One pair of solenoid stops 43 are disposed above each sleeve 26 on the upper level 25, with one stop 43 outside each edge 23 of the beam thickness 15. Similar assemblies 43 (see FIG. 3) are disposed below each sleeve 35 on the lower level 32, one outside each edge 23 of the beam thickness 15. The solenoid stops 43 are used to ensure accurate positioning of the leaves 28, 34 within the fan beam 14 in a manner to be described in more detail below.

Figure 6:
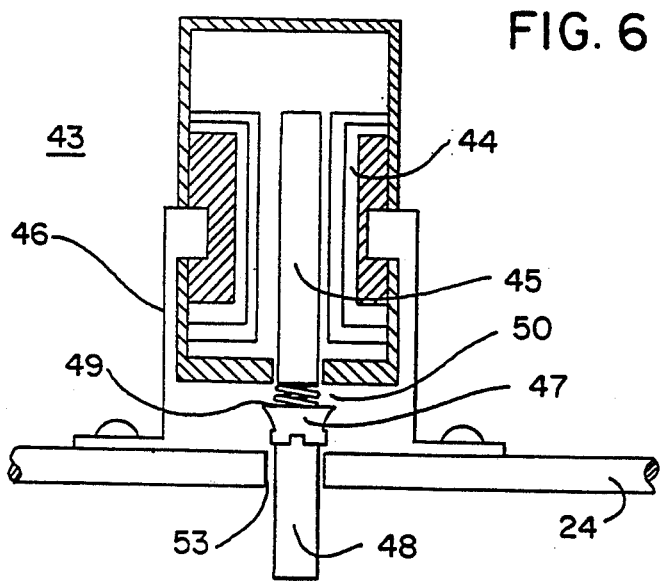
FIG. 6 is a detailed cross sectional view of the solenoid stop assembly shown in FIG. 2 taken along the line 6—6.

Referring to FIG. 6, each stop 43 has an electrical solenoid coil 44 which, when energized, attracts a concentrically located armature 45 against the force of a spring 50. A flexible connector 47 connects the armature 45 to a stopping shaft 48 protruding from the stop 43 to be retracted by the armature when the coil is energized. Each solenoid stop 43 is securely fastened to its respective level of the rack 24 by a mounting bracket 46. A flange 49 on the armature 45 holds the spring 50 between itself and the underside of the coil 45 to bias the stopping shaft 48 out from the stop 43 when the coil 44 is de-energized.

The flexible connector 47 is longitudinally rigid, but laterally flexible to absorb the torque applied to the stopping shaft 48 by impact with its associated leaf 28, 34 as will be described. The stopping shaft 48 is constructed of a rigid but resilient material that will not bend under the pressure of repeated collisions with a collimator leaf 28, 34.

As seen in FIG. 4(b), when the solenoid coil 44 is not energized, the spring 50 biases the armature 45 out from the coil 44 which in turn forces the stopping shaft 48 through a shaft hole 53 in the rack 24, and into the sleeve 26, into the path of leaf movement. When the solenoid coil 44 is energized, the armature 45 retracts into the coil 44 and out of the path of leaf movement.

Referring now to FIGS. 4(a)–(c), during radiation therapy, the stops 43 remain de-energized most of the time with the stopping shafts 48 protruding into the sleeves and thus locking their associated leaf 28 into one of its three steady state positions, the closed position (4(b)) the first open position (4(a)) and the second open position (4(c)).

When a leaf is to move from the first open position (FIG. 4(a)) to the closed position (FIG. 4(b)), the compensator control module 58 first energizes a first solenoid stop 43a which moves a stopping shaft 48a up and out of the sleeve 26 allowing the leaf to move toward the closed position. High pressure air directed to the pneumatic cylinder 39 then pushing the leaf 28 toward the closed position (see FIG. 4(b)). The leaf 28 strikes the second stopping shaft 48b where it is halted in the closed position occluding the entire thickness 15 of the ray 38. Stopping shaft 48(b) ensures the leaf 28 is accurately positioned. The first solenoid stop 43a is then deenergized and the compressively loaded spring 50 expands forcing the stopping shaft 48a down back into the sleeve 26. At this point, the stopping shafts 48a, 48b of both solenoid stops 43a, 43b are within the sleeve 26 and abutting the edges of the leaf 28. With both solenoid stops 43a, 43b de-energized, the leaf 28 is secured in the closed position against perturbing forces.

Similarly, to move the leaf 28 into the second open position, the second stop 43b is energized and the stopping shaft 48b is pulled out of the sleeve 26. The leaf 28 is pushed to the second open position (see FIG. 4(c)). The second stop 43b is de-energized and the stopping shaft 48b is forced into the sleeve 26 to lock the leaf 28 out of the beam.

As will now be described, by alternating open states from one side of the beam thickness 15 to the other, the characteristic gradient attenuation along the thickness 15 of the ray 38 (i.e. the beam 14) can be eliminated.

Figure 8A:
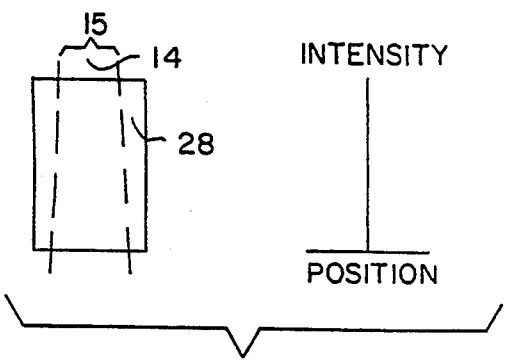
FIG. 8(a)-(g) are graphs showing the changing fluence gradient across the beam as a leaf is moved from a closed state in FIG. 8(a) into a first open state in FIG. 8(c), back into the closed state in FIG. 8(e), into a second open state and again back into the closed state FIG. 8(g).

Referring now to FIG. 8(a), when the leaf 28 is in the closed state, entirely occluding the fan beam thickness 15 the initial cumulative intensity of radiation received by the patient is zero. As the leaf 28 is moving to the first open state (see FIG. 8(b)), the cumulative intensity of the received radiation increases starting with the first areas to be exposed. By the time the leaf 28 reaches the first open state in FIG. 8(c), there is a gradient of received radiation 21 across the beam thickness 15.

Figure 8D:
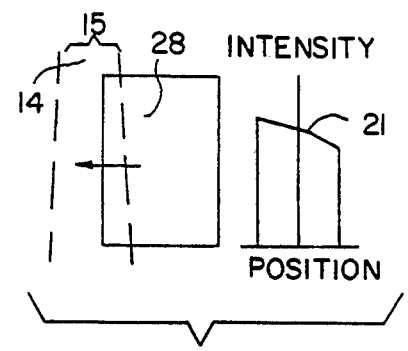
Figure 8B:
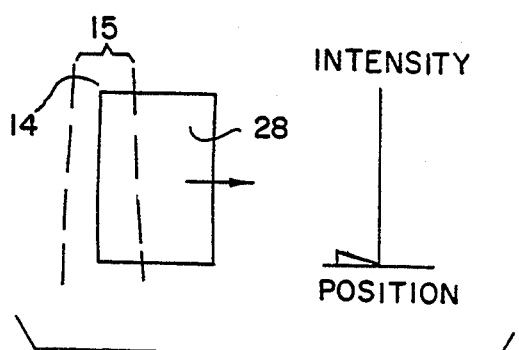
Figure 8E:
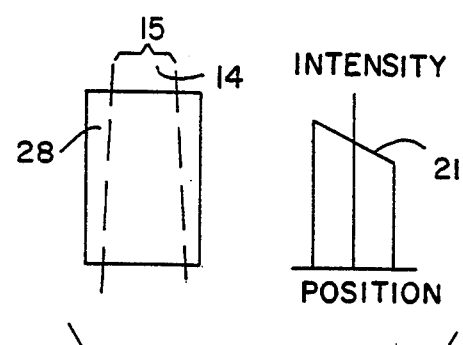
Figure 8C:
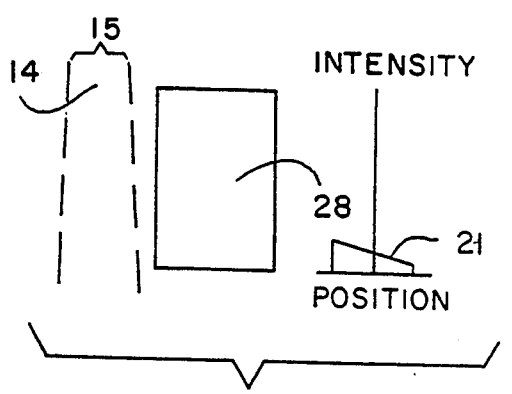
Figure 8F:
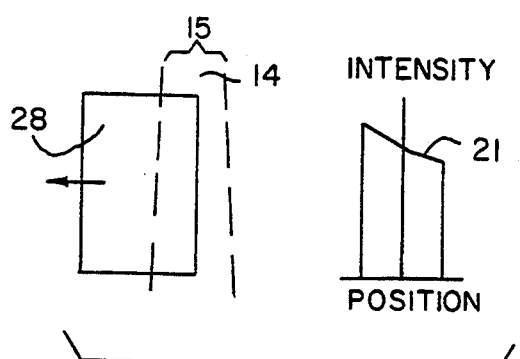
Figure 8G:
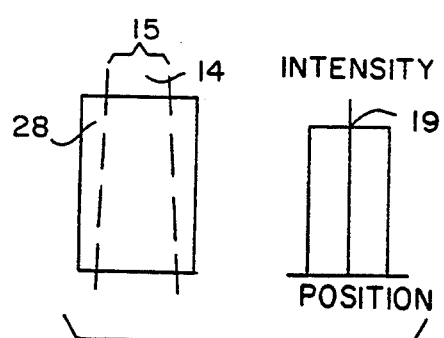

As the leaf 28 begins to return to the closed state as in FIG. 8(d), the gradient attenuation 21 becomes steeper until it is twice as steep as it was after the first open cycle (see FIG. 8(e)).

In the next cycle, the leaf 28 is moved to the second open state as in FIG. 9(f), the exact direction as the previous cycle producing the opposite gradient 21. When the gradients of the two cycles add together, the resulting cumulative intensity 19 of the rays directed across the beam thickness 15 becomes uniform as in FIG. 9(g).

Referring again to FIGS. 4(a)–(c), it should be noted that alternating movement of a leaf 28, results in a uniform radiation exposure across the thickness of the beam 15 only if the velocity of the leaf 28 is constant as the leaf 28 travels through the beam thickness 15. Without a constant leaf velocity, a parabolic exposure profile across the beam thickness 15 results as the exposure of alternating open cycles is added.

While, practically, some acceleration of the leaf 28 as it travels through the beam widths will be acceptable, ideally, most of the acceleration of the leaf 28 will take place while the beam 14 is either fully occluded or entirely unattenuated. Leaf acceleration can be limited to these two conditions by placing the solenoid stop 43 outside the beam thickness 15 and configuring the leaf 28 to be wider than the beam thickness 15 so as to provide for a first 33a and a second 33b acceleration gap on opposite sides of the beam thickness 15.

Referring still to FIGS. 4(a)–(c), when the leaf 28 moves from the first open state (FIG. 4(a)) to the closed state (FIG. 4(b)), it is accelerated from a stationary position to a constant velocity before the leading edge 29 of the leaf 28 passes the first acceleration gap 33a and enters the beam thickness 15. As the leading edge 29 moves across the beam thickness 15 its velocity is constant until it strikes the second stopping shaft 48b. The leaf 28 is decelerated after the leading edge 29 is within the second acceleration gap 33b and the following edge 31 is within the first acceleration gap 33a.

In the closed position (FIG. 4(b)), the leaf 28 occludes the entire beam thickness 15 as well as both acceleration gaps 33a, 33b. Moving from the closed state (FIG. 4(b)), to the second open state (FIG. 4(c)), the leaf 28 is accelerated from its closed stationary position to a constant velocity before the following edge 31 exits the first acceleration gap 33a. Restricting acceleration and deceleration to the period when the leaf edges 29, 31 are within the acceleration gaps is also observed when moving from the second open state to the closed state and from the closed state to the first open state.

It has been found that the optimal acceleration gap 33 size is independent of acceleration potential and is one fourth the beam thickness 15 (see Appendix). Therefore, in order for the leaf 28 to occlude both the beam thickness 15 and both acceleration gaps 33 when in the closed state, the leaf 28 should ideally be constructed 1.5 times as long as the beam thickness 15 (see FIGS. 4(a)–(c)).

Using a leaf 28 that is wider than beam thickness 15 enables the stops 43 to provide a simple leaf deceleration mechanism. When the leaf 28 is moved from its first open state (FIG. 4(a)) to the closed state (FIG. 4(b)), upon impact with the stopping shaft 48b, the leaf 28 may temporarily bounce back off the stopping shaft 48b. Piston pressure is continued to limit "leaf bounce" to positions in which the impacting leaf edge 29 remaining within its associated leaf gap 33b. Thus, leaf deceleration will be limited to acceptable leaf 28 positions.

II. Radiation Therapy Hardware

Figure 5:
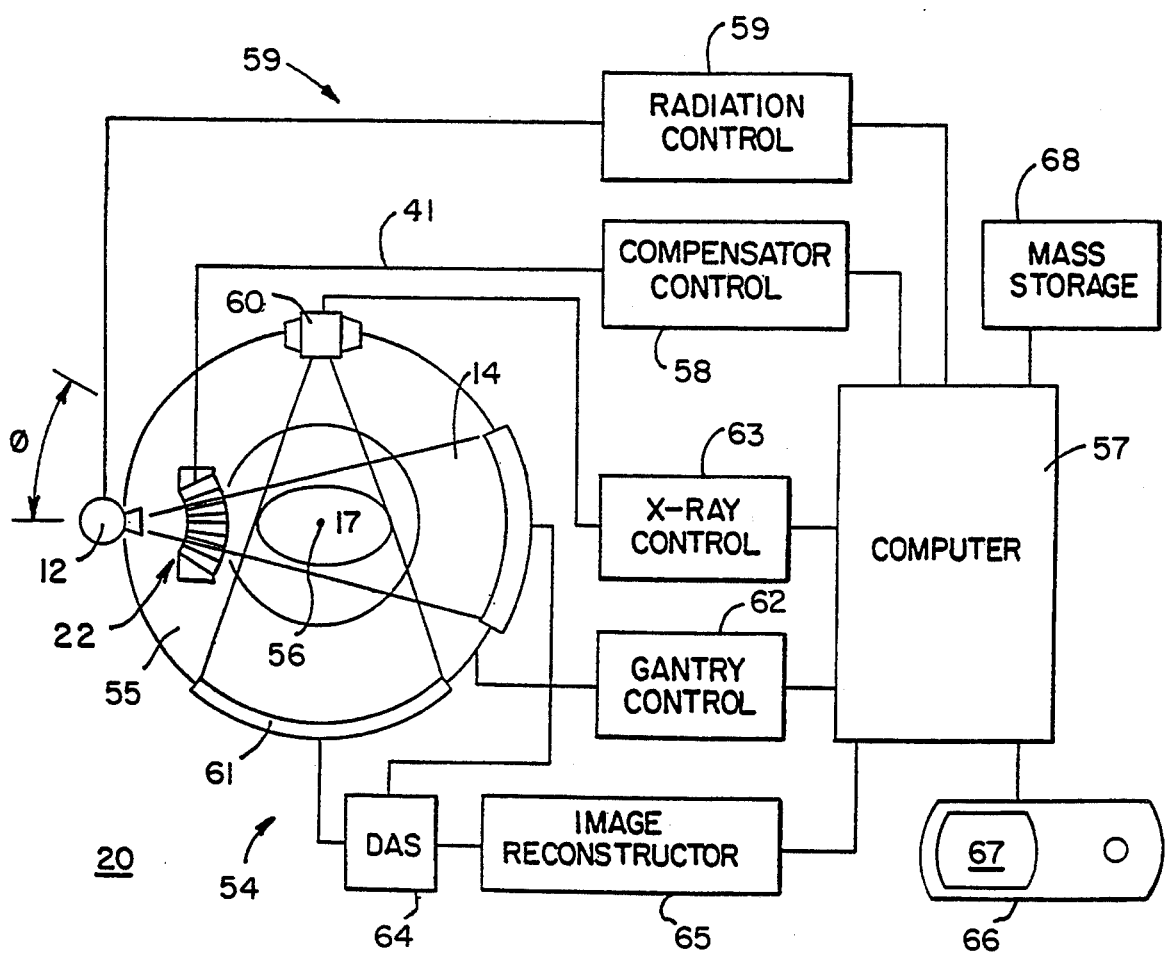
FIG. 5 is a block diagram showing the elements of a radiation therapy apparatus incorporating a conventional CT scanner and the compensator of the present invention and including a computer suitable for controlling that compensator per the present invention.

Referring now to FIG. 5 the radiation source 12 is mounted on a gantry 55, the latter rotating within the fan beam plane 20 about a center of rotation 56 in the patient 17 so that the fan beam 14 may irradiate a slice of the patient 17 from a variety of gantry angles $\theta$.

The radiation source 12 is controlled by a radiation control module 59 which turns the radiation beam 14 on or off under the control of a computer 57.

A compensator control module 58 provides a source of compressed air and valves to gate that air through supply hoses 41 to control, separately, the pneumatic cylinders 39 to move each of the leaves 28, 34 in and out of their corresponding sleeve 26, 35 and associated rays 38 (see also FIG. 1). The compensator control module 58 also controls the solenoid assemblies 43 to energize the solenoid coils 44 allowing the leaves 28, 34 to move between three distinct steady state positions.

Referring again to a tomographic imaging system 54 employing an x-ray source 60 and an opposed detector array 61 may be advantageously mounted on the same gantry 55 as the radiation source 12 to produce a tomographic or slice image of the irradiated slice of the patient 17 prior to radiation therapy for planning purposes. Alternatively, such tomographic imaging may be performed on a separate machine and the slices aligned according to fiducial points on the patient 17.

A gantry control module 62 provides the signals necessary to rotate the gantry 55 and hence to change the position of the radiation source 12 and the angle θ of the fan beam 14 for the radiation therapy, as well as for the computed tomography x-ray source 60 and detector array 61 also attached to the gantry 55. Gantry control module 62 connects with computer 57 so that the gantry may be rotated under computer control and also to provide the computer 57 with a signal indicating the gantry angle θ to assist in that control.

Control modules for the tomographic imaging system 54 include: x-ray control module 63 for turning on and off the x-ray source 60, and data acquisition system 64 for receiving data from the detector array 61 in order to construct a tomographic image. It will be understood to one of ordinary skill in the art that a detector array 61 may also be placed to receive radiation from the radiation source 12 through the patient 17 to assist in verification of the treatment.

An image reconstructor 65 typically comprising a high speed array processor or the like receives the data from the data acquisition system 64 in order to assist in "reconstructing" a tomographic image from such data according to methods well known in the art. The image reconstructor 65 also communicates with computer 57 to assist in high speed computations used in the present invention as will be described below. The tomographic image allows verification of the patient setup just prior to radiation therapy treatment.

A terminal 66 comprising a keyboard and display unit 67 allows an operator to input to programs and data to the computer 57 and to control the radiation therapy and tomographic imaging equipment 59 and 54 and to display tomographic images produced by the image reconstructor 65 on the display 67. A mass storage system 68, being either a magnetic disk unit or tape drive, allows the storage of data collected by the tomographic imaging system 54 for later use.

Computer programs for operating the radiation therapy system 59 will generally be stored in mass storage unit 68 and loaded into the internal memory of the computer 57 for rapid processing during use of the system 59.

During operation of the radiation therapy unit 59, the compensator control module 58 receives from the computer 57 a fluence profile for each gantry angle. The fluence profile describes the intensity or fluence of each ray 38 of the radiation beam 14 from the radiation source 12 that is desired for that gantry angle θ at a given position of the patient support table (not shown) as translated through the radiation beam 14. Together, the fluence profiles for each gantry angle make up a treatment sinogram for a particular position of the patient table.

The compensator control module 58 moves the leaves 28, 34 of the compensator 22 rapidly between their open and closed states to either fully attenuate or provides no attenuation to each ray 38. Gradations in the fluence of each ray, as needed for each fluence profile, are obtained by adjusting the relative duration during which each leaf 28, 34 is in the closed position compared to the relative duration during which each leaf 28, 34 is in the open position, for each gantry angle. The ratio between the closed and open states or the "duty cycle" for each leaf 28, 34 affects the total energy passed by a given leaf 28, 34 at each gantry angle and thus controls the average fluence of each ray 28. The ability to control the average fluence at each gantry angle permits accurate control of the dose provided by the radiation beam 14 through the irradiated volume of the patient 17 by therapy planning methods to be described below.

The fluence profiles of the treatment sinogram are determined by therapy planning software (described below) and stored in the computer 57.

III. Therapy Planning Software

The generation of a treatment sinogram needed to obtain the full benefits of the above described compensator is performed by specially developed software running on the computer 57 and reconstructor 65. Although the treatment planning is performed in software, it will be recognized that the planning may also be implemented in discrete electronic circuitry dedicated to this operation and that such dedicated circuitry may be employed to provide even greater speed to this process.

Figure 7A:
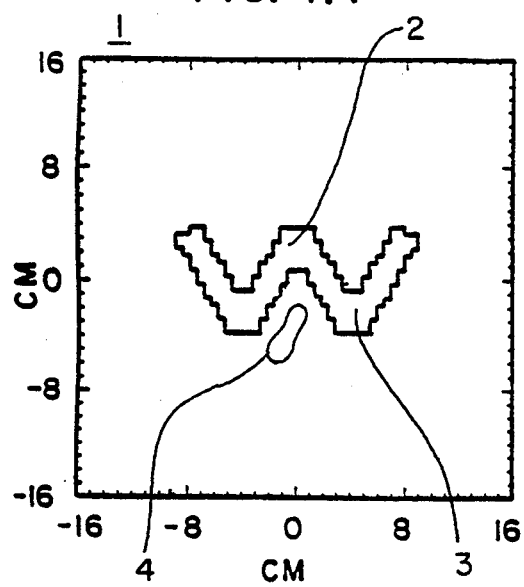
FIGS. 7(a)-(d) are dose distributions of a hypothetical tumorous region showing dose intensity by lines of equal dose, with FIG. 7(a) showing a desired dose distribution and FIGS. 7(b), (c), and (d) showing progressive actual dose distributions after two, three and ten iterations per present invention.

Referring to FIG. 7(a), the generation of the desired treatment sinogram to control compensator 22 begins with the definition of a desired dose map 1. A typical desired dose map 1 assigns a relatively high radiation dose, within a dose constraint, to an area of tumorous tissue 2 and a second lower radiation dose to the area of healthy tissue 3 outside of that region. The healthy tissue 3 may include an area 4 including a radiation sensitive organ or the like to which an even lower radiation dose may be assigned.

The desired dose map 1 is stored within the memory of computer 57 as an array of elements each element holding one digital value, and may be most easily entered by displaying the tomographic view of the slice of patient 17 on the display 67 of the terminal 66 and manually tracing around the tumorous area 2 using of a trackball or similar input device as is well understood in the art. Standard area-filling computer programs may be used to transfer the dose values assigned to each traced region to the appropriate element in the array of memory representing the desired dose map 1.

Each element of the dose map 1 thus defines the dose desired at each of the plurality of volume elements 74 ("voxels") within a slice of the patient 17. Referring to FIG. 9, each voxel 74 of the patient 17 may be identified by a vector $\vec{r}$ defined from a given reference point 76. The dose at each voxel 74 is $D(\vec{r})$.

A. Converting Dose to Terma

1. Terma

Generally, the dose at any voxel $\vec{r}$ will depend on the energy received at that voxel $\vec{r}$ from radiation scattered from adjacent voxels $\vec{r}'$ (where adjacent voxels $\vec{r}'$ include the voxel $\vec{r}$, i.e., the radiation received directly from the radiation source 12). The dose $D(\vec{r})$ for a given voxel $\vec{r}$ is given by the following formula:

$$D(\vec{r}) = \int T(\vec{r}')A(\vec{r}-\vec{r}')d^3\vec{r}' \quad (1)$$

where $T(\vec{r}')$ is a value indicating the magnitude of the primary total energy released from $\vec{r}'$ per unit mass of that voxel $\vec{r}'$ and is called the "terma" (total energy released per unit mass).

For a monoenergetic external radiation source, the terma rate $\dot{T}(\vec{r})$ is described by:

$$\dot{T}(\vec{r}) = \frac{\mu}{\rho}(\vec{r})E\int \dot{\phi}(\vec{r})dt \quad (2)$$

where $\mu/\mu$ is an effective mass attenuation value at the voxel $\vec{r}$, E is the energy of the radiation photons in Joules, $\Phi$ is the distribution of the fluence rate (flux density). The integration of energy times fluence rate over time is energy fluence $\Psi(\vec{r}')$ where:

$$\Psi(\vec{r}) = E \int \Phi(\vec{r}) dt \qquad (3)$$

hence $$T(\vec{r}) = \frac{-\mu}{\rho} (\vec{r}) \Psi(\vec{r}) \qquad (4)$$

Equation (4) basically relates how much energy from the ray 38 interacts with the voxel r'.

2. Convolution Kernel $A(\vec{r}-\vec{r}')$ is a convolution kernel describing non-stochastic energy transport or scattering in a uniform medium. $A(\vec{r}-\vec{r}')$ thus describes how the energy from each voxel $\vec{r}'$ spreads to contribute to the dose at voxel $\vec{r}$.

The kernel $A(\vec{r}-\vec{r}')$ may be generated using a Monte Carlo method as is generally understood in the art. As mentioned, it is a three-dimensional function indicating the fraction of energy absorbed at voxel $\vec{r}$ per unit of energy released at voxel $\vec{r}$. The energy emitted from the terma of each voxel $\vec{r}'$ finds it source in a directed ray 38 from external radiation source 12 and thus A(e,rar/r/$-\vec{r}'$) generally anisotropic as suggested in FIG. 10, spreading outward away from the entry of ray 38. Energy conservation requires that:

$$\int A(\vec{r}) d^3\vec{r} = 1.0 \qquad (5)$$

That is, if the energy transferred by the primary interaction were all deposited on the interaction point, the kernel would be approximated as a delta function. Referring still to FIG. 10, the anisotropy of $A(\vec{r}-\vec{r}')$ is related to the gantry angle 8 and thus of the angle of incidence of the ray 38 at $\vec{r}'$. If the gantry angles $\theta$ at which the patient 17 is irradiated are predetermined, a multidirection convolution kernel $B(\vec{r}-\vec{r}')$, shown in FIG. 12, may be created from weighted superimposition of the kernels A ($\vec{r}-\vec{r}'$).

Referring to FIG. 11, assuming that the spreading of radiation is approximately equal for all beam directions and the rays 38 from each gantry angle $\theta$ contribute equally to the terma at $\vec{r}$, then the multidirectional convolution kernel reduces to a "isotropic" form as follows:

$$B(\vec{r}-\vec{r}) = \frac{1}{n} \sum_{i=1}^{n} A(\vec{r}-\vec{r})_i \qquad (6)$$

where n is the number of discrete gantry angles from which rays 38 are projected.

For multiple rays 38 at different gantry angles, the total dose at a given voxel $\vec{r}$ is the sum of doses from each constituent beam is therefore:

$$D(\vec{r}) = \int T(\vec{r}) B(\vec{r}-\vec{r}) d^3\vec{r} \qquad (7)$$

where $T(\vec{r}') = nT(\vec{r})_i$, the latter term being the contributed portion of the terma for the ith gantry angle.

This simplification assumes that the contribution to the terma from each ray 38 is equivalent and takes advantage of the distributive property of convolution. Errors in this assumption are reduced by the filtration to be discussed later.

Equation (7) substantially simplifies the calculation of dose from terma but still requires a convolution for each voxel $\vec{r}$ times the total number of voxels $\vec{r}'$ to calculate the dose over the entire patient volume. Preferably, therefore, the calculational efficiency of the fast Fourier transform can be used and equation (7) converted to the following:

$$D(\vec{r}) = F^{-1}\{F\{T(\vec{r})\} \cdot F\{B(\vec{r}-\vec{r})\}\} \qquad (8)$$

where F and $F^{-1}$ symbolize Fourier and inverse Fourier transforms respectively. This simplification of equation (8) requires that the kernel $B(\vec{r}-\vec{r}')$ be spatially invariant and relies on the convolution theorem which states that convolution of two spatially invariant quantities in a space domain is equivalent to multiplication in the frequency domain.

The assumption of the spatial invariance of $B(\vec{r}-\vec{r}')$ is correct only to a first order approximation. Typically, the kernel $B(\vec{r}-\vec{r}')$ for an external radiation source 12 is a complex function of: (1) beam hardening of a polyenergetic x-ray beam (i.e., the effect of the filtration of the patient 17 in increasing the proportion of high frequency or high energy radiation components), (2) the number of rays 38 crossing each voxel, and (3) exponential attenuation by the patient mass.

In the preferred embodiment, this first factor, beam hardening, is neglected because it is an effect smaller than the attenuation problem. Thus, the photon energy spectrum in the patient 17 may be assumed to be the same as that of the external radiation source 12. This simplification is not required, however, and it will be understood that beam hardening could be accurately accounted for by representing a photon energy spectrum by a finite number of separately convolved energy intervals.

The second factor, the difference in the number and orientation of rays 38 that cross each voxel, caused by the geometry of a finite number of gantry angles and the fan orientation of the beam 14, affect spatial invariance. Problems arising from the fan orientation of the beam (in contrast to a parallel beam geometry) are largely solved if there is a full rotation of the gantry 55. Errors resulting from the fact that irradiation is performed at only a finite number of gantry angles have been determined to be acceptable.

The third factor affecting the assumption of spatial invariance is the attenuation of the medium. This affects the fractional contribution of the total terma from the beams at each gantry angle. Accordingly, in those steps of the planning procedure, as will be noted below, where accurate calculation of dose is critical, the dose distribution is calculated separately for each beam based on the attenuation of overlying voxels, such attenuation deduced from the parameters of the tomographic image. In this case the simplification of equation (8) may not be employed and repeated convolutions must be performed. In certain steps in the planning process, however, as will be noted, an estimate is sufficient and in these cases $B(\vec{r}-e,rar/r/\,')$ is assumed to be spatially invariant and the dose calculated according to equation (8).

Production of terma values from a desired dose map 1 is then simply the process of inverting equation (8) as follows:

$$T(\vec{r}) = F^{-1}\left(\frac{F\{D(\vec{r})\}}{F\{B(\vec{r}'-\vec{r})\}}\right) \quad (9)$$

This inversion requires that there be no significant "zeros" (typically at high frequencies) in the denominator term F{B(e,rar/r/ −r′)} or more simply that the kernel B(r−e,rar/r/ ′) be spatially compact (i.e., the Fourier transform of a spatially compact kernel will have significant high frequency content). It has been determined by the present inventors that the kernels dictated for patients 17 are sufficiently compact to allow this Fourier deconvolution.

Figure 12:
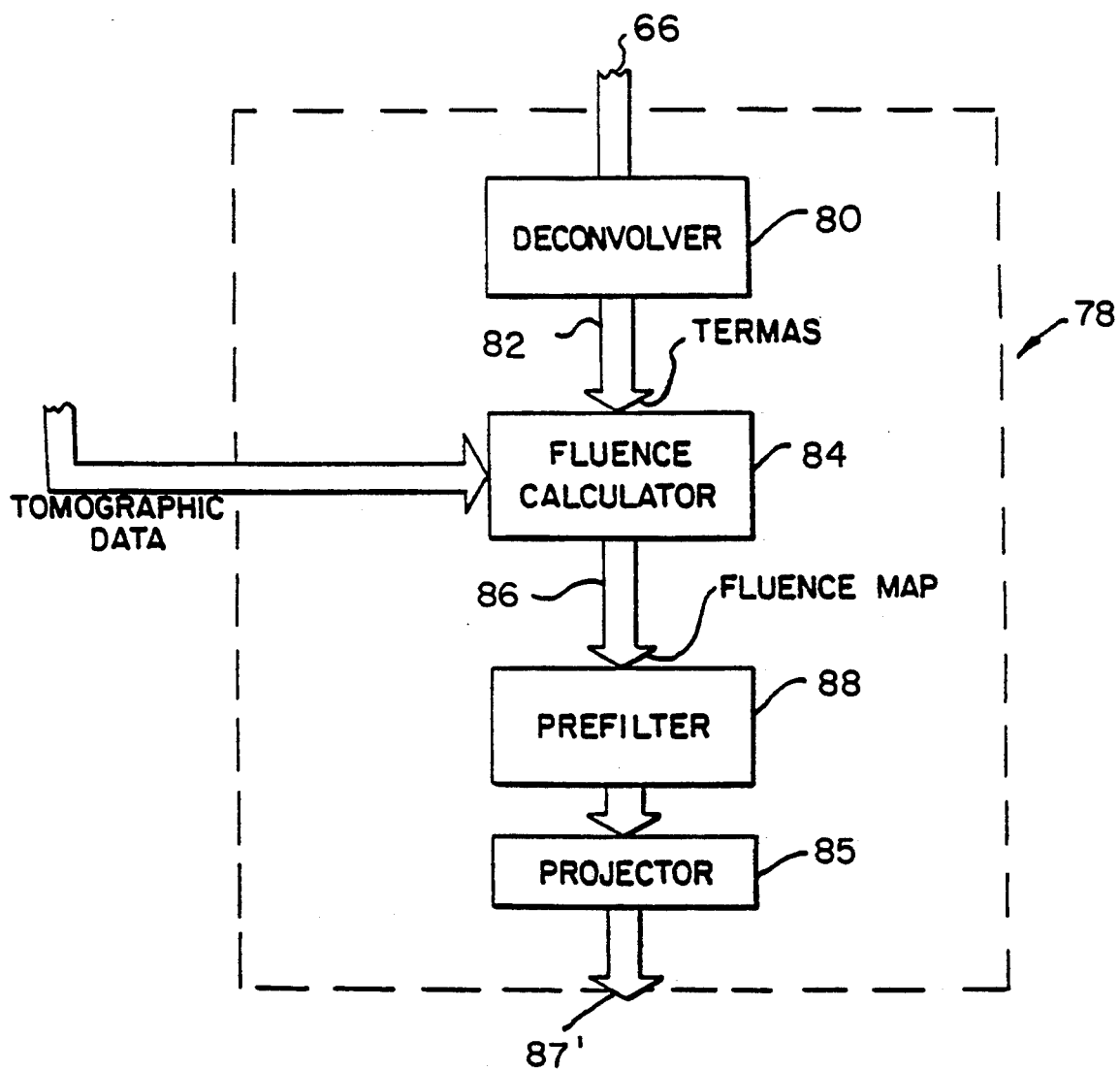
FIG. 12 is a block diagram depicting the fluence profile calculator which takes a desired dose map and calculates a fluence profile.

Referring now to FIG. 12, this deconvolution to produce a terma map 82, giving the terma for each $\vec{r}$, from the desired dose map 1, is represented by process block 80.

B. Converting Terma to Voxel Energy Fluence

Knowing the terma map 82, the energy fluence Ψ(e,-rar/r/ ′), which is a measure of the beam intensity, can be determined at each corresponding voxel by equation (4) from a knowledge of μ/ρ as follows:

$$\Psi(\vec{r}) = \frac{T(\vec{r})}{\frac{\mu}{\rho}(\vec{r})} \quad (10)$$

The value of μ/ρ may be estimated and considered a constant or actual μ/ρ may be deduced from the tomographic scan data collected by means of the tomographic imaging system 11, (shown in FIG. 5). In this manner and as illustrated by process block 84 of FIG. 12, a fluence map giving the fluence at each point of the terma map may be determined.

C. Converting Voxel Energy Fluence to Energy Fluence Profile

The energy fluence Ψ(r′) at each voxel r̄′ is related to the energy of the ray 38 exiting the compensator 22 by the relation:

$$\Psi(\vec{r}) = \Psi_0(\phi,\theta)\, e^{-\int \mu/\rho(\vec{r})\rho(\vec{r})\,\epsilon(p\,-\,\hat{r}\cdot\vec{r})dt}\left(\frac{SSD^2(\phi,\theta)}{|\vec{t}|^2}\right) \quad (11)$$

where $\Psi_O(\Phi,\hat{t})$ is the energy fluence for a given ray 38 as described by δ(p−t̂·r) at the exit of the compensator 22 and serves to define the fluence profile of the compensator and θ and Φ are the gantry angle and the offset angles of the ray 38 as previously described.

The exponential term represents the attenuation of the ray 38 from the exit of the compensator 22 to the voxel r̄ caused by the mass of the patient 17 where by μ/ρ(e,rar/r/ ) is the attenuation for each voxel r̄ along the ray 38, ρ(r̄) is the density of each r̄, SSD (Φ,θ) is the distance between the exit of the compensator 22 and the surface of the patient 17, t̂ is a unit vector along r̄ (where the origin of is now assumed to be the center of rotation of the gantry 57), and p is the perpendicular distance from the gantry's center of rotation 56 and the ray 38. The vector is simply a vector along the ray 38 to provide an integration variable.

The fluence at each voxel r̄ is related to the fluence of the radiation beam 14 emitted from the compensator 22 by equation (11). In the preferred embodiment, the density and attenuation of each r̄, μ/ρ(r̄) and ρ(r̄) are assumed to be constant and the fan beam of radiation is approximated by a parallel beam, hence $$\frac{SSD^2(\phi,\theta)}{|\vec{t}|^2} = 1$$

Borrowing from the mathematics of tomographic image reconstruction, the fluence map 86 may be "reverse" back projected (i.e. projected) by projector 85 to determine a fluence profile to be produced by the external source necessary to generate the desired fluence map and hence dose.

This projection is simply the opposite of a typical back projection used to form an image of a tomographic slice of a patient 17 from a series of projections taken in a tomographic imaging system. Because a projection is a line integral across a distribution, the energy fluence distribution for each voxel (equation (11)) is first differentiated with respect to the rayline t̂:

$$\frac{d\Psi(\vec{r})}{dt} = \left[\frac{\mu}{\rho}(\vec{r})\rho(\vec{r})\epsilon(p\,-\,\hat{r}\cdot\vec{r}) + \frac{2}{t}\right]\Psi(\vec{r}) \quad (12)$$

The line integral of $$\frac{d\Psi(\vec{r})}{dt}$$

along t̂, corrected for attenuation and inverse-square fall off, then represents the projection operation and $\Psi_O(\Phi\theta)$, the fluence profile over the offset angles Φ of each gantry angle θ, is:

$$\Psi_0(\phi,\theta) = \int \left[\frac{\mu}{\rho}\vec{r}\rho(\vec{r})\epsilon(p\,-\,\hat{r}\cdot\vec{r}) + \frac{2}{t}\right] \times \left(\Psi(\vec{r})\, e^{+\int \mu/\rho(\vec{r})\rho(\vec{r})\delta(p\,-\,\hat{r}\cdot\vec{r})dt}\left(\frac{|\vec{t}|^2}{SSD^2(\phi,\theta)}\right)\right) \rightleftharpoons \delta(p\,-\,\hat{r}\cdot\vec{r})dt^2 \quad (13)$$

The projection of equation (13) is represented by projector 85 in FIG. 12.

The projection process, for the purpose of computing fluence profiles of the compensator 22, differs in a fundamental way from the simple inverse of tomographic back projection. The difference is primarily in a concern for the sharpness in the transition of the dose between the irradiated tumorous tissue 2 and the healthy tissue 3. Sharpness in this transition region reduces the irradiation of healthy tissue 3 and is preferred over actual fidelity of the dose to the desired dose map 1.

For this reason, the fluence map 86 from the fluence calculator 84 is prefiltered as shown by process block 88 to produce a filtered fluence map Ψ′(Φ,θ) as follows:

$$\Psi'(\Phi,\theta) = F^{-1}\{F\{\Psi(\Phi,\theta)|\omega|\}\}_+ \quad (14)$$

where Ψ(Φ,θ) is the fluence map 86 and |ω| is a ramp filter in frequency space and the '+' subscript indicates the positive component of the filtering result. This prefilter 88 serves to increase the high frequency content of the fluence map 86 and thus to aid in rapid transition of dose at the tumor/non-tumor interface.

It is noted that this prefilter 88 is similar to the filter used in tomographic imaging's "filtered" back projection. That is, like tomographic imaging, the filter de-emphasizes the low frequency components of the projection in producing image data. In addition other prefilters may be applied to correct for the use of the radially symmetric kernel (equation (6)) in computing the dose map from the terma map composed from the fluence profile.

In practice the computation of a terma map, the generation of a fluence map and the calculation of the fluence profiles need not be performed as discrete steps but may be accomplished by a direct projection of the dose map with appropriate filtering. The filtering is accomplished by a "fast inversion filter" which combines in projection space the operation of deconvolution and ramp filtration.

This may be symbolically specified by the following equation $$\Psi(\Phi,\theta) = \rho\{D(\vec{r})\} \otimes I(t) \quad (15)$$

where $\rho$ refers to a projection operation and $I(t)$ is the fast inversion filter. The $\otimes$ operators refers to a convolution operation such as would normally be done in Fourier space using a fast Fourier transformation.

Referring still to FIG. 12, the fluence profile calculations of block 78, including the deconvolver 80, the fluence calculator 84, the prefilter 88 which includes any projection space filter (such as a ramp filter, a fast inversion filter followed by truncation of zeros), and the projector 85 thus produce fluence profiles which together create an estimated treatment sinogram 87' from the desired dose map 1. The fluence profile calculator 78 may use the Fourier convolution of equation (9) in the estimate of the fluence profiles at this stage, accepting minor inaccuracies in that process, to be corrected at a later stage, as will be described below.

D. Iteration

Figure 13:
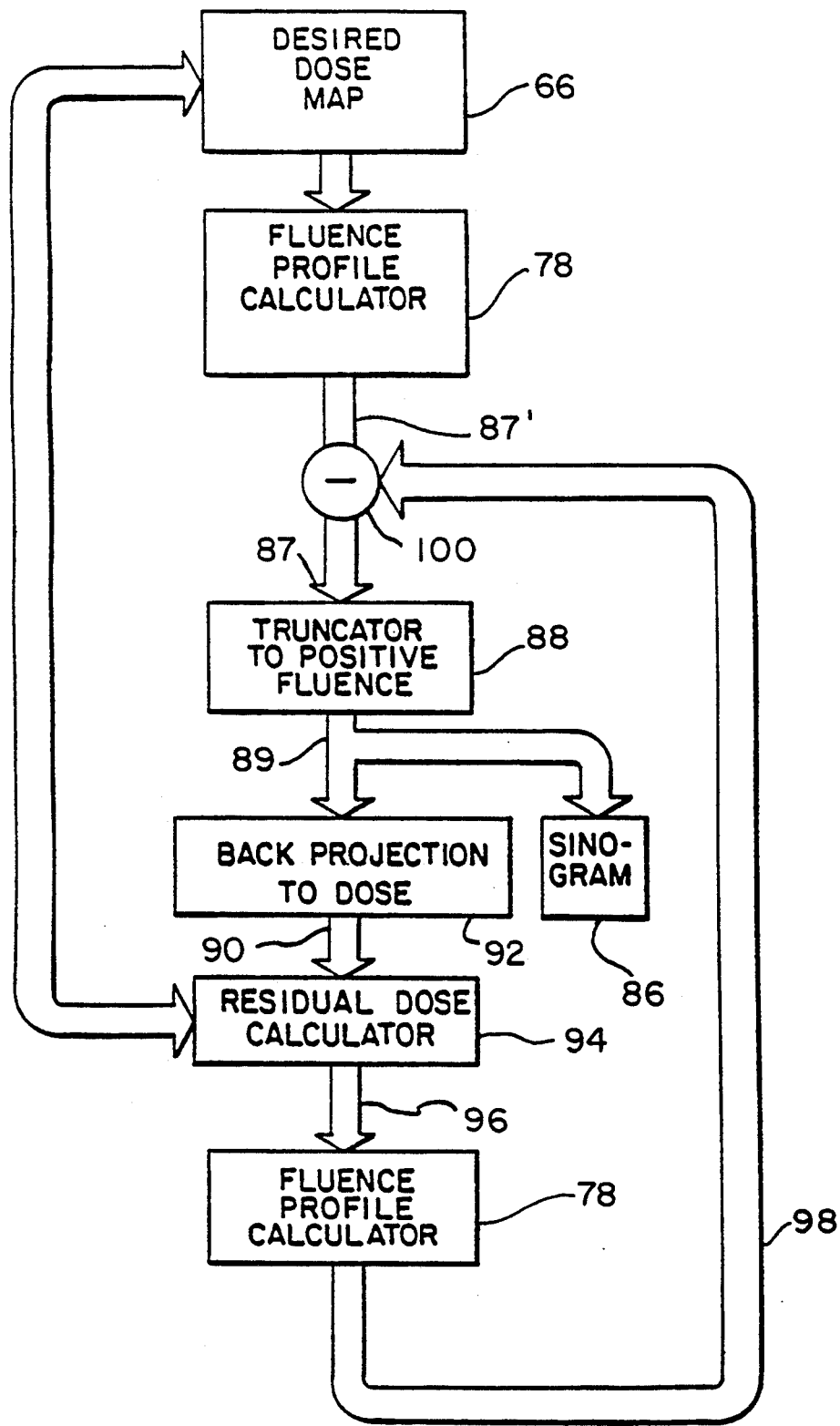
FIG. 13 is a block diagram depicting the overall iterative method of controlling the compensator of the present invention, employing the fluence profile calculation method of FIG. 12.

Referring now to FIG. 13, the fluence profile calculator 78 converts the desired dose map 1 to an estimated treatment sinogram 87' however the fluence profiles of this estimated treatment sinogram 87' may not be used to control the compensator 22 because, in general, the estimated treatment sinogram 87 will include positive and negative values of fluence. Only positive values of fluence are physically realizable by the compensator 22; a negative value of fluence would represent a ray 38 that absorbed radiation along its path which is physically unrealizable.

Accordingly, at process block 88, the fluence values of the estimated treatment sinogram 87' are truncated to positive fluence values 89. As a result of this truncation, the estimated treatment sinogram 87' no longer produces the desired dose map.

The amount of error resulting from the truncation producing the positive fluence profiles 89 is determined by back projecting the positive fluence values 89 to an actual dose map 90 deviating from the desired dose map 1. This back projection is accomplished by computing a fluence map from the positive fluence values 89 per equation (11) and a terma map per equation (4) and then convolving the terma map with the kernel per equation (7) to establish the actual dose map 90 per process block 92 of FIG. 13.

In this back projection, the assumption of spatial invariance of the convolution kernel $B(\vec{r}-\vec{r}')$ is not made so as to produce a more accurate actual dose map 90.

The projection of a fluence profile onto a patient 17 to compute a dose map may be performed by a number of other procedures known to those of ordinary skill in the art.

The actual dose map 90 is compared to the desired dose map 1 to produce residual dose map 96 as indicated by process block 94. In the preferred embodiment, the comparison subtracts from the values of each voxel $\vec{r}$ of the actual dose map 90, the greater of: a) the corresponding value of desired dose map 1, or b) a predetermined upper dose constraint. The predetermined upper dose constraint is a threshold number that is deemed an acceptable dose to tumorous tissue 68. Clearly, other methods of quantifying the difference between the desired dose map and the actual dose map will be apparent from this description to those of ordinary skill in the art.

Figure 14A:
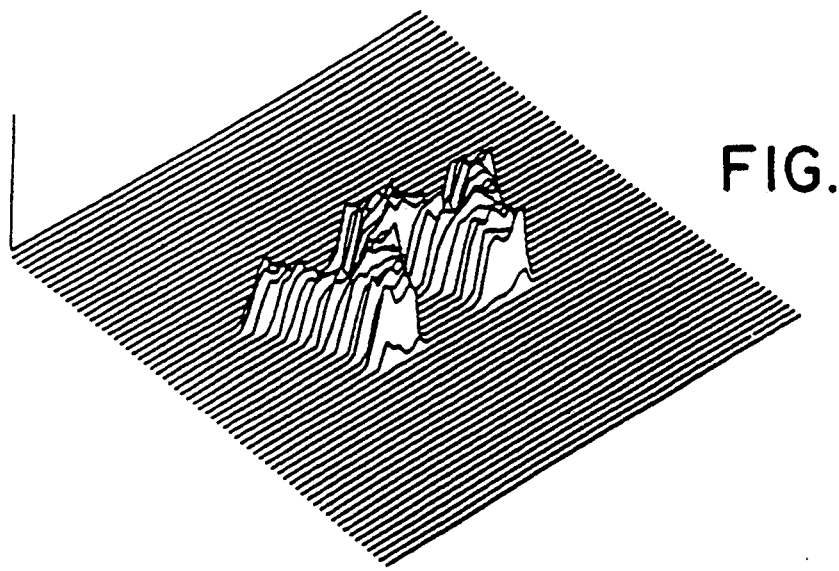
FIGS. 14(a)-(c) are perspective views of plots showing the error between the desired dose distribution and the actual dose distribution obtained with the present invention for one, two and four steps of iteration respectively.

The result of this comparison process 94 is to produce a residual dose map 96 shown in FIG. 14(a). This residual dose map 96 is then, again, operated on by the fluence profile calculator 78 (in lieu of the desired dose map 66) to produce an error fluence profile 98 (in lieu of the estimated treatment sinogram 87).

A thus produced error fluence profile 98 is subtracted by subtracter 100 from the estimated treatment sinogram 87' to produce a new estimated treatment sinogram 87.

Figure 14B:
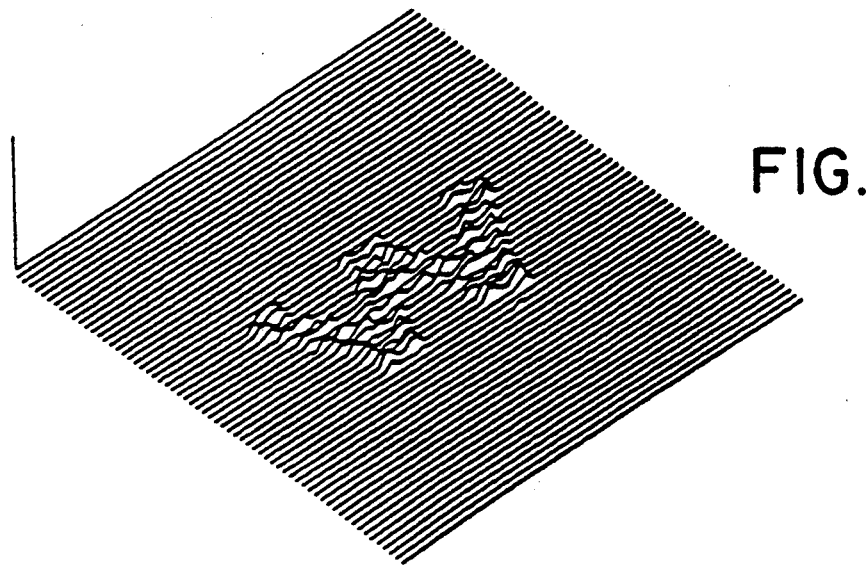
Figure 14C:
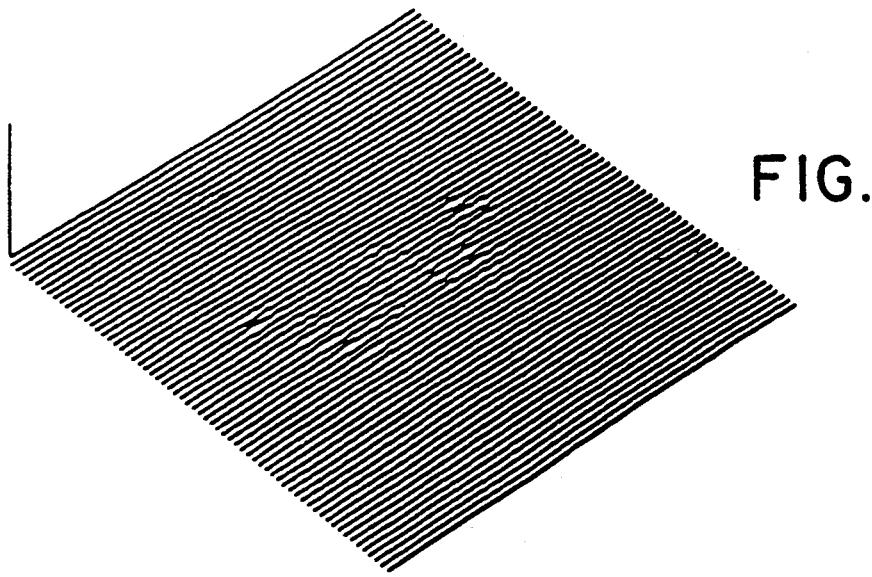

As shown in FIG. 13, this new estimated treatment sinogram 87 is repeatedly operated on by process block 88, 92, 94 and 78 for a predetermined number of iterations, the magnitude of the error fluence profile 98 values decreasing with each iteration as shown in FIGS. 14(b)–(d) until a suitably low error fluence profile 98 is obtained.

The new estimated fluence profile 87 is then truncated per process block 88 to produce a final sinogram 91 for use in controlling the compensator 22 as previously described.

Figure 7B:
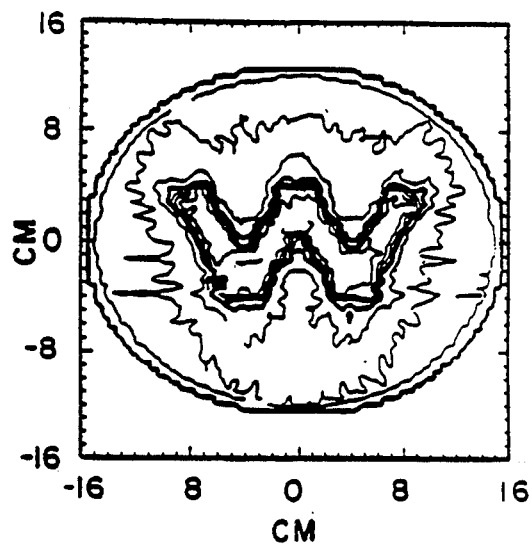
Figure 7C:
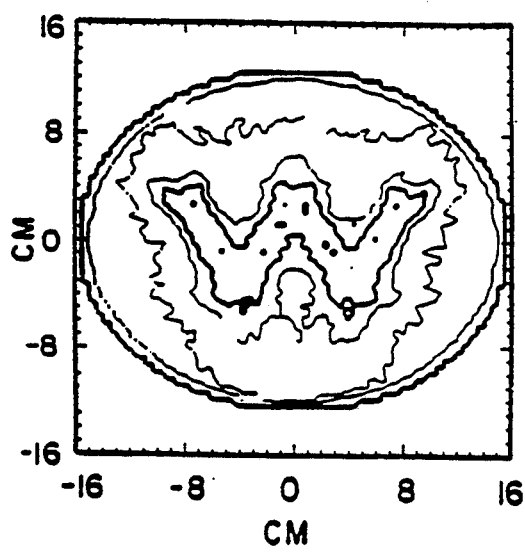
Figure 7D:
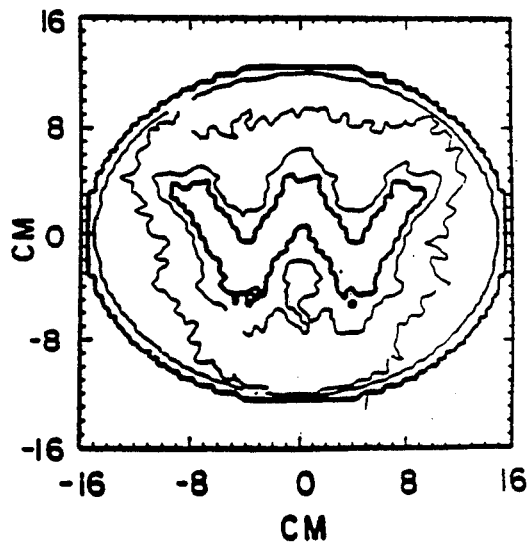

Referring again to FIGS. 7(b), (c) and (d), dose maps obtained by the present invention corresponding to a desired dose map 1 of FIG. 7(a) are shown after: one iteration (FIG. 7(b)); two iterations (FIG. 7(c)); and ten iterations (FIG. 7(d)). The variations in dose in the target volume shown in FIG. 7(d) are plus or minus 2% about the predetermined upper limit of 1,000 cGy.

The above description has been that of a preferred embodiment of the present invention. It will occur to those who practice the art that many modifications may be made without departing from the spirit and scope of the invention. For example, a computed tomography system need not be incorporated with the radiation therapy equipment but separate such equipment could be used. The relationship between the terma values and the fluence values may assume a constant density of the patient to eliminate the need for a precise tomographic scan of the irradiated area. Clearly the method for planning radiation therapy is not limited to a particular radiation source but may be used with any radiation source which may be decomposed into separately attenuated radiation rays.

It should also be recognized that the pneumatic cylinders 39 could be constructed to decelerate the leaves 28, 34 and limit the effect of "leaf bounce" and leaf wear upon stopping shaft collisions during leaf movement between states. Referring again to FIGS. 4(a)–(c), when leaf 28 is moved from the first open state (FIG. 4(a)) to the closed state (FIG. 4(b)), once the leading edge 29 is through the beam thickness 14, the associated pneumatic cylinder 39 could produce a breaking pulse that slows the leaf 28 before the leading edge 29 impacts the stopping shaft 48b. Similar deceleration pulses could be utilized at the end of each leaf movement to limit leaf and stopping shaft wear. In order to apprise the public of the various embodiments that may fall within the scope of the invention, the following claims are made:

Appendix

Acceleration and The Optimum Acceleration Gap

Treatment planning assumes a number of discrete beams with defined intensities at given gantry angles. In fact, the radiation treatment is done on a continuous basis with constant gantry rotation. For the leaf collimator to produce irradiation approximating a set of discrete beams, the leaf cycle time must be small compared to the time required for the gantry to move between the angles of the theoretical discrete beams. The time for that gantry movement $t_{beam}$ is given by:

$$t_{beam} = \frac{T\Delta Z}{LB} \quad (1)$$

where T is the total treatment beam-on time, $\Delta Z$ is the slice thickness at the isocenter, L is the length of the field (being the sum of many slices) and B is the number of discrete gantry angles for a full rotation (this corresponds to the number of projections angles in CT data acquisition).

The minimum beam intensity that can be delivered (other than having the leaf closed for all of time $t_{beam}$) depends on the minimum switching time $\Delta t$ which is the time it takes to open the field and immediately close it. For fastest switching, the closing time should be the same as the opening time. If the velocity of collimator motion is constant then there can be more uniformity in the field as shown in FIG. 9(c). The average beam intensity during switching is ½ of the intensity when the beam is open. A constant velocity means the collimator has to accelerate up to the required velocity before the field is exposed.

The minimum switching time is made up of three components:
1. The time it takes to accelerate up to velocity.
2. The time it takes the collimators to completely cross the field.
3. The time to decelerate to zero velocity.

With a constant acceleration magnitude, the deceleration time is equal to the acceleration time.

The minimum intensity is given by the following equation:

$$\Phi_{min} = 2\frac{\dot{\Phi}_0}{2} t_{cross} + 2\dot{\Phi}_0 t_{accel} \quad (2)$$

where $\dot{\Phi}_0$ is the fluence rate when the collimator is open, $t_{cross}$ it the time it takes the collimator to cross the open field and $t_{accel}$ is the time it takes the collimator to accelerate up to a constant velocity (or decelerate to rest). For a constant crossing velocity v and acceleration a, times $t_{cross}$ and $t_{accel}$ are described by simple kinematic ratios. Equation 2 becomes:

$$\Phi_{min} = \dot{\Phi}_0 \left( \frac{\Delta z}{v} + 2\frac{v}{a} \right) \quad (3)$$

where $\Delta z$ is the physical distance of the collimator jaws. This can be expressed in terms of the slice thickness $\Delta Z$ projected to the isocenter.

$$\Delta z = \frac{SCD}{SAD} \Delta Z \quad (4)$$

where SCD is the source-to-collimator distance and SAD is the source-to-axis distance. If equation 3 is differentiated with respect to the velocity it is possible to solve for the optimal velocity $v_{opt}$:

$$v_{opt} = \sqrt{\frac{\Delta z a}{2}} \quad (5)$$

Substituting for the optimal velocity, the minimum intensity $\Phi_{min}$ is given by:

$$\Phi_{min} = \dot{\Phi}_0 \sqrt{\frac{8\Delta z}{a}} \quad (6)$$

The maximum fluence delivered at a discrete beam position is just the product of the fluence rate $\dot{\Phi}_0$ and the time per beam $t_{beam}$ as follows:

$$\Phi_{min} = \dot{\Phi}_0 \frac{T\Delta Z}{LB} \quad (7)$$

The ratio of minimum fluence to maximum fluence is the ratio of Equation 6 to 7:

$$\frac{\Phi_{min}}{\Phi_{max}} = \sqrt{\frac{8\Delta z}{a}} \frac{LB}{T\Delta Z} = \sqrt{\frac{8 \cdot SCD}{SAD \cdot \Delta Z \cdot a}} \frac{LB}{T} \quad (8)$$

The optimal switching time $t_{opt}$ is given by:

$$t_{opt} = 2\frac{\Delta z}{v_{opt}} + 2\frac{v_{opt}}{a} \quad (9)$$

Substituting in $v_{opt}$ yields the following:

$$t_{opt} = 3\sqrt{\frac{2\Delta Z}{a}} \quad (10)$$

Observe that the optimal switching time is the time to completely open the field with a constant velocity, decelerate with a constant acceleration to rest, and immediately reserve the action to close the field such that there is a minimum amount of fluence emitted during this sequence.

The optimal distance through which the constant acceleration takes place before the collimator crosses the beam is given by:

$$z_{opt}' = \frac{v_{opt}^2}{2a} = \frac{\Delta z}{4} \quad (11)$$

Therefore, referring to FIGS. 4(a)-(c), the acceleration gap 33($z'_{opt}$) on either side of the fan beam thickness 15 should be one fourth the thickness of the fan beam 15. Note that the optimal distance $z'_{opt}$ is independent of acceleration.

We claim:

1. In a radiation therapy machine having a radiation source for producing a radiation beam directed toward a patient at a gantry angle, the beam including a plurality of adjacent rays, a compensator comprising:
   a plurality of radiation attenuating leaves;
   a supporting structure for guiding the leaves between:
   a closed state centered within the radiation beam, the leaf thus occluding one ray of the beam;
   a first open state with the leaf displaced outside of the radiation beam on a first side of the one ray; and
   a second open state with the leaf displaced outside of the radiation beam on a second side of the one ray;
   motivation means for independently moving each leaf alternately between the open and closed state and between the closed and second open states; and
   timing means communicating with the motivation means for controlling the ratio of the period of time during which each leaf is in the closed state to the period during which each leaf is in one of the first and second open states to control the average fluence of each ray of the beam.

2. The compensator as recited in claim 1 wherein the motivation means is a plurality of pneumatic cylinders connected by linkages to individual leaves to move the leaves.

3. The compensator as recited in claim 1 where the beam diverges from a focal spot in a fan shape and the leaves are wedge shaped to have adjacent faces defining planes intersecting a common line through the focal spot.

4. The compensator as recited in claim 1 wherein the motivation means slides the leaves along guide rails on each side of the leaves and wherein the leaves include notches for receiving the guide rails.

5. The compensator as recited in claim 1 wherein the timing means receives a value indicating the angle of the gantry and changes the ratio as a function of this angle.

6. The compensator as recited in claim 1 including a stop for stopping the leaves in the closed state after movement from the first and second open states.

7. The compensator as recited in claim 6 wherein the stop includes two solenoid assemblies together having armatures movable to abut a first and second side of the leaf when the leaf is in the closed state.

8. The compensator as recited in claim 1 wherein the leaf in the first open and second open states are spaced away from the beam by a predetermined acceleration distance.

9. The compensator as recited in claim 8 wherein the acceleration distance is equal to $\frac{1}{4}$ a beam thickness measured along the path of movement of the leaf.

10. The compensator as recited in claim 9 wherein a leaf width measured along the path of movement of the leaf, is $1\frac{1}{2}$ times as long as the beam thickness.

11. In a radiation therapy machine having a radiation source for producing a radiation beam directed toward a patient at a gantry angle, the beam including a plurality of adjacent rays, a compensator comprising:
    a first plurality of radiation attenuating leaves; and
    a second plurality of radiation attenuating leaves;
    a first supporting structure for guiding the first plurality of leaves between a closed state, each leaf thus occluding every other ray of the beam, and an open state outside of the radiation beam;
    a second support structure for guiding the second plurality of leaves between a closed state, each leaf thus occluding those rays of the beam not occluded by the first plurality of leaves when the latter are in the closed state, and an open state outside of the radiation beam wherein the first plurality of leaves in the closed state are positioned closer to the radiation source than the second plurality of leaves in the closed state;
    motivation means for independently moving each leaf between the open and closed states; and
    timing means communicating with the motivation means for controlling the ratio of the period of time during which each leaf is in the closed state to the period during which each leaf is in the open state to control the average fluence of each ray of the beam.

12. The compensator as recited in claim 11 wherein the motivation means is a plurality of pneumatic cylinders connected by linkages to individual leaves.

13. The compensator as recited in claim 11 where the beam diverges from a focal spot in a fan shape and the leaves are wedge shaped to have adjacent faces defining planes intersecting a common line through the focal spot.

14. The compensator as recited in claim 11 wherein the motivation means slides the leaves along guide rails on each side of the leaves and wherein the leaves include notches for receiving the guide rails.

15. The compensator as recited in claim 11 wherein the timing means receives a value indicating the angle of the gantry and changes each ratio as a function of this angle.

16. The compensator as recited in claim 11 including a stop for stopping the leaves in the closed state after movement from the first and second open states.

17. The compensator as recited in claim 16 wherein the stop includes two solenoid assemblies together having armatures movable to abut a first and second side of the leaf when the leaf is in the closed state.

* * * * *

UNITED STATES PATENT AND TRADEMARK OFFICE
CERTIFICATE OF CORRECTION

Patent No.   : 5,351,280                                   Page 1 of 3

Dated        : September 27, 1994

Inventor(s)  : Stuart Swerdloff, et al.

It is certified that error appears in the above-identified patent and that said Letters Patent is hereby corrected as shown below:

Column 4, line 36, "FIG." should be --FIGS.--.

Column 10, line 54, "$\vec{r}is$" should be --$\vec{r}$ is--.

Column 11, line 7, "$\psi(\vec{r}) = \overline{E} \int \dot{\phi}(\vec{r}) dt$" should be --$\psi(\vec{r}) = E \int \dot{\phi}(\vec{r}) dt$--.

Column 11, line 27, "$\vec{r}$" should be --$\vec{r}'$--.

Column 11, lines 29-30, "A(e,rar/r/-$\vec{r}'$) generally" should be --A($\vec{r}-\vec{r}'$) is generally--.

Column 11, lines 38-39, a new paragraph should begin with the word "Referring".

Column 11, line 40, "angle 8" should be --angle θ--.

Column 11, line 49, "at $\vec{r}$" should be --at voxel $\vec{r}'$--.

Column 12, line 63, "B($\vec{r}$-e,rar/r/')" should be --B($\vec{r}-\vec{r}'$)--.

Column 13, line 8, "F{B(e,rar/r/ -$\vec{r}$)}" should be --F{B($\vec{r}-\vec{r}'$)}--.

Column 13, line 9, "B($\vec{r}$-e,rar/r/ ')" should be --B($\vec{r}-\vec{r}'$)--.

UNITED STATES PATENT AND TRADEMARK OFFICE
CERTIFICATE OF CORRECTION

Patent No.    : 5,351,280
Dated         : September 27, 1994
Inventor(s)   : Stuart Swerdloff, et al.

It is certified that error appears in the above-identified patent and that said Letters Patent is hereby corrected as shown below:

Column 13, line 16, "each $\vec{r}$" should be --each voxel $\vec{r}$--.

Column 13, lines 21-22, "ψ(e,-rar/r/')" should be --$\psi(\vec{r}')$--.

Column 13, line 35, "map giving" should be --map 86 giving--.

Column 13, Equation (11),

"$\psi(\vec{r}) = \psi_0(\phi,\theta) e^{-\int \mu/\rho(\vec{r})\rho(\vec{r}) \epsilon(p-\hat{r}\cdot\vec{r})\, d\vec{t}} \left( \overrightarrow{-\frac{SSD^2(\phi,\theta)}{|\vec{c}|^2}} - \right)$" should be --

$\psi(\vec{r}') = \psi_0(\phi,\theta) e^{-\int \mu/\rho(\vec{r})\delta(p-\hat{r}\cdot\vec{r})\, d\vec{t}} \left( \frac{SSD^2(\phi,\theta)}{|\vec{c}|^2} \right)$--.

Column 13, line 54, "$\psi_0(\phi,¼)$" should be --$\psi_0(\phi,\theta)$--.

Column 13, line 62, "μ/ρ(e,rar/r/)" should be --$\mu/\rho(\vec{r})$--.

Column 13, line 63, "each $\vec{r}$" should be --each voxel $\vec{r}$--.

Column 14, Equation (12),

"$\frac{d\psi(\vec{r})}{dt} = \left[ \frac{\mu}{\rho}(\vec{r})\rho(\vec{r})\epsilon(p-\hat{r}\cdot\vec{r}) + \frac{2}{t} \right] \psi(\vec{r})$" should be --

$\frac{d\psi(\vec{r})}{dt} = \left[ \frac{\mu}{\rho}(\vec{r})\rho(\vec{r})\rho(\vec{r})\delta(p-\hat{r}\cdot\vec{r}) + \frac{2}{t} \right] \psi(\vec{r})$--.

UNITED STATES PATENT AND TRADEMARK OFFICE
CERTIFICATE OF CORRECTION

Patent No.  : 5,351,280
Dated       : September 27, 1994
Inventor(s) : Stuart Swerdloff, et al.

It is certified that error appears in the above-identified patent and that said Letters Patent is hereby corrected as shown below:

Column 14, Equation (13), part of which appears in column 13 should all be in column 14, $$"\psi_0(\phi,\theta) = \int \left[\frac{\mu}{\rho}(\vec{r})\,\rho(\vec{r})\,\epsilon(\rho-\hat{r}\cdot\vec{r}) + \frac{2}{t}\right]$$

$$\times \left(\psi(\vec{r})\,e^{+\int \mu/\rho(\vec{r})\,\rho(\vec{r})\,\delta}\,(\rho-\hat{r}\cdot\vec{r})\,dt\left(\frac{|\vec{c}|2}{SSD2}(\phi,\theta)\right)\right.$$

$$\doteq \delta(p-\hat{r}\cdot\vec{r})\,d\vec{t}",\ \text{should be,}$$

$$-- \psi_0(\phi,\theta) = \int \left[\frac{\mu}{\rho}(\vec{r})\,\rho(\vec{r})\,\delta(\rho-\hat{r}\cdot\vec{r}) + \frac{2}{t}\right]$$

$$\times (\psi(\vec{r})\,e^{+\int \mu/\rho(\vec{r})\,\rho(\vec{r})\,\delta(\rho-\hat{r}\cdot\vec{r})}\,d\vec{t}\left(\frac{|\vec{c}|2}{SSD2}(\phi,\theta)\right)\cdot$$

$$\doteq \delta(p-\hat{r}\cdot\vec{r})\,d\vec{t}\ --$$

Column 14, line 49, "profiles of the" should be --profiles for the--.

Signed and Sealed this

Twenty-fourth Day of January, 1995

Attest:

BRUCE LEHMAN

*Attesting Officer*                         *Commissioner of Patents and Trademarks*